(12) United States Patent
Park et al.

(10) Patent No.: US 10,765,566 B2
(45) Date of Patent: Sep. 8, 2020

(54) ABSORBENT ARTICLE WITH PARTIALLY SEPARABLE, SKIN-CONTACTING TOPSHEET LAYER

(71) Applicant: Kimberly-Clark Worldwide, Inc, Neenah, WI (US)

(72) Inventors: JaeEun Park, Yongin-Si (KR); Franz Aschenbrenner, Kastl (DE); Caishan Tan, Yongin-Si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 654 days.

(21) Appl. No.: 15/540,212

(22) PCT Filed: Dec. 30, 2014

(86) PCT No.: PCT/US2014/072785
§ 371 (c)(1),
(2) Date: Jun. 27, 2017

(87) PCT Pub. No.: WO2016/108856
PCT Pub. Date: Jul. 7, 2016

(65) Prior Publication Data
US 2017/0354550 A1 Dec. 14, 2017

(51) Int. Cl.
*A61F 13/15* (2006.01)
*A61F 13/20* (2006.01)
(Continued)

(52) U.S. Cl.
CPC ........ *A61F 13/5116* (2013.01); *A61F 13/472* (2013.01); *A61F 13/512* (2013.01); *A61F 2013/51186* (2013.01)

(58) Field of Classification Search
CPC ................ A61F 13/512; A61F 13/5123; A61F 2013/5127; A61F 2013/5128; A61F 13/5116; A61F 13/472; A61F 2013/51186
See application file for complete search history.

(56) References Cited

U.S. PATENT DOCUMENTS 5,007,906 A    4/1991   Osborn et al.
5,324,278 A    6/1994   Visscher et al.
(Continued)

FOREIGN PATENT DOCUMENTS

AU        703676 B2    4/1999
CN       1193269 A     9/1998
(Continued)

*Primary Examiner* — Michele M Kidwell
(74) *Attorney, Agent, or Firm* — Kimberly-Clark Worldwide, Inc.

(57) ABSTRACT

An absorbent article has a longitudinal direction, a transverse direction, and a depth direction and includes absorbent article opposing first and second longitudinal ends, and absorbent article opposing lateral side edges extending between the absorbent article opposing first and second longitudinal ends. The absorbent article comprises a liquid permeable first topsheet layer having first topsheet layer opposing lateral side edges, and first topsheet layer opposing longitudinal ends as well as a liquid permeable second topsheet layer subjacent to the liquid permeable first topsheet layer. The liquid permeable second topsheet layer has second topsheet layer opposing lateral side edges, and second topsheet layer opposing longitudinal ends, and is attached at or along two opposing attachment zones to the liquid permeable first topsheet layer along or adjacent the first topsheet layer opposing lateral side edges.

20 Claims, 9 Drawing Sheets

(51) Int. Cl.
*A61F 13/511* (2006.01)
*A61F 13/512* (2006.01)
*A61F 13/472* (2006.01)

(56) References Cited

U.S. PATENT DOCUMENTS

| | | | |
|---|---|---|---|
| 5,342,343 A | 8/1994 | Kitaoka et al. | |
| 5,624,421 A | 4/1997 | Dabi et al. | |
| 5,827,258 A | 10/1998 | McFall et al. | |
| 5,853,403 A | 12/1998 | Tanzer et al. | |
| 6,042,575 A | 3/2000 | Osborn, III et al. | |
| 6,171,291 B1 | 1/2001 | Osborn, III et al. | |
| 6,222,092 B1 | 4/2001 | Hansen et al. | |
| 6,293,935 B1 | 9/2001 | Kimura et al. | |
| 6,296,628 B1 | 10/2001 | Mizutani | |
| 6,371,948 B1 | 4/2002 | Mizutani | |
| 6,423,043 B1 | 7/2002 | Gustafsson | |
| 6,471,682 B2 | 10/2002 | Kashiwagi | |
| 6,858,771 B2 | 2/2005 | Yoshimasa et al. | |
| 6,955,667 B1 | 10/2005 | Tanaka et al. | |
| 7,160,278 B2 | 1/2007 | Mizutani et al. | |
| 7,465,297 B2 | 12/2008 | Watanabe et al. | |
| 7,648,490 B2 | 1/2010 | Kuroda et al. | |
| 7,722,587 B2 | 5/2010 | Suzuki et al. | |
| 7,763,001 B2 | 7/2010 | Kawamura | |
| 7,976,525 B2 | 7/2011 | McDaniel | |
| 2002/0072726 A1* | 6/2002 | Mishima | A61F 13/4942 604/385.22 |
| 2002/0120247 A1 | 8/2002 | Mizutani et al. | |
| 2003/0050614 A1 | 3/2003 | D'Acchioli et al. | |
| 2005/0027278 A1 | 2/2005 | Mizutani et al. | |
| 2006/0135930 A1 | 6/2006 | Mizutani et al. | |
| 2008/0065038 A1* | 3/2008 | Sugiyama | A61F 13/49473 604/385.04 |
| 2012/0283680 A1 | 11/2012 | Zander et al. | |
| 2015/0313766 A1* | 11/2015 | Miao | A61F 13/512 604/385.101 |
| 2017/0354549 A1* | 12/2017 | Cho | A61F 13/472 |

FOREIGN PATENT DOCUMENTS

| | | |
|---|---|---|
| CN | 1053566 C | 6/2000 |
| EP | 1 048 277 A2 | 11/2000 |
| JP | 01-122727 U | 8/1989 |
| JP | 2002-315776 A | 10/2002 |
| JP | 2007-167191 A | 7/2007 |
| KR | 2001-0071415 A | 7/2001 |
| WO | WO 2014/085974 A1 | 6/2014 |
| WO | WO 2014/191921 A1 | 12/2014 |

* cited by examiner

ABSORBENT ARTICLE WITH PARTIALLY SEPARABLE, SKIN-CONTACTING TOPSHEET LAYER

FIELD OF THE INVENTION

The present invention is generally directed to absorbent personal care articles. In particular, the present invention is directed to feminine and adult hygiene absorbent personal care articles, and their associated skin-contacting layers (or topsheets), as well as methods for producing such articles.

BACKGROUND OF THE INVENTION

Feminine and adult hygiene absorbent personal care articles are often used to protect consumer undergarments and outergarments from soiling, and to collect and retain body exudates such as menses, blood, or urine. Such articles are most commonly placed in the crotch region of undergarments during use. In the context of such products, absorbency and comfort are two main product attributes and areas of concern for the wearers of such articles. In particular, wearers are often interested in knowing that such products will sufficiently absorb body exudates in order to protect their garments, or bedsheets from staining. Wearers are also interested in having such products demonstrate reduced feelings of wetness once a product has been soiled or insulted during use. Unfortunately, once such a product has been soiled, the topsheet layer (i.e. user-facing, skin-contacting surface layer of the article) often remains wet or at least feels wet for some time throughout the period of use. The topsheet layer may frequently be absorbent, being made so from hydrophilic construction materials, such as natural fibers or surfactant-treated polymeric materials. While such materials may be soft to the touch, these materials often retain at their surface some noticeable moisture following soiling, thereby creating an uncomfortable sensation throughout their continued use. While in an ideal situation, such articles are replaced by the user once soiling actually occurs, in some instances the user may not initially recognize that soiling has occurred. Upon such realization, the user may not be in a location where a change of product is possible or convenient. The frequent replacement of these articles may also be impractical given a user's particular daily activities.

As a result of the desire of consumers to experience a reduced wetness sensation from a product during prolonged use (for both skin-health rationale as well as physical comfort), manufacturers have explored numerous technological approaches to address these feelings following product insult. Manufacturers have attempted to reduce both the initial feelings of wetness and also continuing sensations of "rewet". For the purposes of this application, the term "rewet" refers to the propensity of personal care absorbent articles to absorb fluid or liquid such as menses or urine through the topsheet layer and deliver it to an interior absorbent layer, and subsequently, to release it under the continuing pressure of wear, back to the topsheet layer from the absorbent layer(s). This release of liquid back to the topsheet often leads to the consumer perception of continuing wetness.

Absorbent article manufacturers have specifically designed individual topsheet layers for reduced wetness, based on chemical enhancements to the topsheet layer. In this regard, hydrophobic topsheet layers have been developed from inherently hydrophobic, polymeric fibrous nonwoven materials or apertured film materials, such that the article demonstrates an extended feeling of dryness. Absorbed fluid that is retained in absorbent layers subjacent these topsheet layers may have less of a propensity to pass back through the topsheet layer to the user's skin, as a result of hydrophobic surface properties of the topsheet. In some instances, the topsheet layer acts as a one-way valve, allowing moisture to pass in one direction and keeping it below the user-facing, skin contacting surface.

Such topsheet designs have included relatively small or larger openings to allow for the direct passage of fluid to an underlying absorbent layer. For example, AU 703676 to Nomura et al. describes a topsheet layer that is attached to a pad's longitudinal ends and transverse side edges, with an exposed central opening, to allow for fluid to pass into the product. While such designs have been somewhat successful in creating a longer consumer feeling of dryness, there is still a need for products which offer increased breathability and air circulation, and increased consumer confidence and perception that such product will physically separate the user from the fluid of the absorbent layer(s) and less likelihood that the consumer will actually experience a continuing feeling of wetness, either as a result of initial soiling or rewet. Further, hydrophobic, film-based topsheets with relatively larger openings, have often created an uncomfortable, "plastic"—like feel for the products, and there is a continuing need to address this undesirable sensation.

Manufacturers have also developed multicomponent topsheet layers in which the layer incorporates different materials at different regions across the user-facing, skin-contacting surface. In such layers, a first material can either be side-by-side with a second material along a product central longitudinal direction, or alternatively, can surround a second different material, as seen for example, in JP 1-122727U. Such layers include two materials generally within the same X-Y plane, and which have been designed in-part for the consumer to feel different sensations at a centrally located, fluid-deposition region (or insult region) on the article, compared to at the article peripheral edges. In such designs for example, apertured polymeric films may be placed in the centrally located region with softer nonwoven materials placed at the peripheral side edges. In some patent references, such multicomponent topsheet layers are described as being placed above a centrally apertured subjacent layer, when viewed along the product depth direction, such as for example in international publication WO 2014/085974 to Miao Lin et al. However, even with such so-called, "dual-cover" or "bicomponent" topsheets, there is still a need for increased breathability and air circulation in absorbent articles, and for physical separation of the topsheet layer from the underlying absorbent layers so as to reduce rewet possibilities.

Since hydrophobic and multicomponent topsheet layers have only offered a partial solution to the initial wetness or continuing rewet sensations, absorbent article manufacturers have also explored more complex structural solutions, as opposed to individual layer or material design, to address the wetness sensations and consumer concerns. For example, manufacturers have created fluid distribution systems to more rapidly or effectively transfer fluid away from the initial fluid insult region of an article topsheet. However, such systems have not satisfactorily addressed surface retention of fluid/liquid in topsheet layers, nor assisted in physically separating the topsheet layers from underlying soiled structures.

Manufactures have therefore also designed structures to physically separate initially soiled regions of an article, from the one or more subjacent absorbent layer(s), or to otherwise isolate the absorbed fluid in the absorbent article from the fluid deposition area. Such physical separation has often been accomplished at greater cost and article complexity, through the use of rigidifying spacing layers or structures. Spacing layers may be seen for example, in U.S. Pat. No. 5,324,278 to Visscher et al., which describes use of a spacing or separating structure positioned between a topsheet and subjacent absorbent core layer, and U.S. Pat. No. 6,296,628 to Mizutani and U.S. Pat. No. 7,160,278 Mizutani et al., which describe a compound-like pad in which an upper spaced absorbent structure is positioned over a lower absorbent pad structure. In such compound pads, the raised topsheet layer is still maintained immediately adjacent or attached to an absorbent layer, thereby allowing moisture to potentially re-contact a user's skin during continued use. Such raised layers may also sacrifice user-comfort, as the user is having to feel relatively rigid protrusions in the female perineal area during use.

Other elevated liquid handling layers have been designed for a variety of absorbent articles in order to create a spatial gap between an underlying absorbent layer and a user-facing liquid handling layer. In U.S. Pat. No. 5,853,403 to Tanzer et al., such an apertured, liquid handling elevated layer is illustrated. Such layer is connected at the layer and article longitudinal ends (and in some examples along the lateral side edges), but is designed to handle a relatively large amount of liquid. Further additional auxiliary or floating structures are illustrated in JP2007167191 to Tanaka and United States Publication 20050027278 to Mizutani et al. However, these structures either encompass multiple additional materials that necessitate additional and costly manufacturing steps, encompass a variety of attachment mechanisms, or alternatively position an upper, user-facing surface immediately adjacent an additional, relatively high capacity, liquid handling or absorbent layer. Therefore, there is still a need for an absorbent article which physically separates a topsheet layer from an absorbent layer, without reliance on additional and costly intermediate layers or structure, and as a result, reduces rewet and encourages breathability/air circulation through the article while in use. There is a further need for an absorbent article in which liquid or other body exudate can travel unimpeded directly from a user through an absorbent article topsheet layer to a lower separated, absorbent portion of the absorbent article, with reduced contact with a user's skin.

SUMMARY OF THE INVENTION

In accordance with one embodiment of the invention, an absorbent article has a longitudinal direction, a transverse direction, and a depth direction. The absorbent article includes absorbent article opposing first and second longitudinal ends, and absorbent article opposing lateral side edges extending between the absorbent article opposing first and second longitudinal ends. The absorbent article comprises a liquid permeable first topsheet layer having first topsheet layer opposing lateral side edges, and first topsheet layer opposing longitudinal ends. The absorbent article further comprises a liquid permeable second topsheet layer subjacent, along the absorbent article depth direction, to the liquid permeable first topsheet layer, the liquid permeable second topsheet layer having second topsheet layer opposing lateral side edges, and second topsheet layer opposing longitudinal ends, and being attached at or along two opposing attachment zones to the liquid permeable first topsheet layer, along or adjacent the first topsheet layer opposing lateral side edges. The attachment zones may comprise adhesive, ultrasonic, or thermal bonding mechanisms and may optionally include one or more folds. The liquid permeable first topsheet layer is unattached to the liquid permeable second topsheet layer at the first topsheet layer opposing longitudinal ends. Additionally, a continuous unattached area or areas are present at least partially across the absorbent article transverse direction between the two opposing attachment zones, the first and second liquid permeable topsheet layers being unattached from one another at the continuous unattached area or areas. Such unattached area or areas allow the two topsheet layers to physically separate from one another during product use, thereby at times, forming a spatial gap or void space between them. Desirably such unattached area or areas extends for the full length of the first topsheet layer, such that there is a potential for an extended void space or spatial gap to be formed between the two topsheet layers along the article longitudinal direction when such topsheets separate as a result of their structure or article lateral compression by a user. Desirably in one embodiment, such topsheet layers are only attached to each other at or adjacent the opposing lateral side edges of the first topsheet layer. Further, in one alternative embodiment, such absorbent article includes no other layer or layers between the first and second topsheet layers along the article depth direction.

The absorbent article further includes a liquid impermeable backsheet layer and at least one absorbent core layer sandwiched between the liquid permeable second topsheet layer and the liquid impermeable backsheet layer along the absorbent article depth direction. The liquid permeable first topsheet layer is apertured such that there is at least one uninterrupted aperture opening extending through the entire thickness of the liquid permeable first topsheet layer, to the liquid permeable second topsheet layer to provide a direct liquid or exudate passageway from the user to the upper surface of the second topsheet layer. Such aperture is a macro-aperture opening, such that it allows the uninterrupted flow of liquid through the first topsheet layer to the second topsheet layer as well as the visualization of the second topsheet layer through the first topsheet layer. Desirably, in one embodiment, such aperture opening is circular, having a diameter of at least 2 mm. Alternatively, such aperture opening(s) is much larger, such as to include a length of between about 30 mm and 100 mm, and a width of between about 20 mm and 60 mm. Further, it is desirable in one embodiment, that the liquid permeable second topsheet layer be relatively more hydrophilic than the liquid permeable first topsheet layer. Alternatively, it is desirable that the liquid permeable first topsheet layer be hydrophobic and the liquid permeable second topsheet layer be hydrophilic. For example, in one embodiment, such liquid permeable first topsheet layer is fashioned from polyolefinic nonwoven, film, or nonwoven-film laminate sheets. In a further embodiment, such liquid permeable second topsheet layer is fashioned from a hydrophilic polyolefinic, through-air bonded carded web.

In an alternative embodiment, the liquid permeable first topsheet layer includes a bend or fold line along the absorbent article longitudinal direction, desirably along the central longitudinal direction/axis. Such bend or fold line allows the liquid permeable first topsheet layer to bend upward with respect to the liquid permeable second topsheet layer. Such bend resembles an inverted "V" configuration with the point facing upward towards the user. In another alternative embodiment, the bend or fold line is an embossed line that is present on one or both side surfaces (the upper or lower surfaces) of the liquid permeable first topsheet layer. In still another alternative embodiment, the bend line is either a continuous line or a discontinuous embossment line, alternatively a continuous or discontinuous arrangement of relatively small embossment shapes arranged generally in a line along the central longitudinal direction. In one embodiment, such embossment lines or shapes have a width along the article transverse direction of between about 1 mm and 3 mm. In still a further alternative embodiment, at least one uninterrupted aperture opening through the first topsheet layer entire thickness, is positioned along the bend line, which is in one embodiment, along the central longitudinal direction/axis.

In still a further alternative embodiment, the liquid permeable first topsheet layer includes multiple, similarly sized and shaped uninterrupted aperture openings through the layer entire thickness. In one such embodiment, such multiple aperture openings are proximately located towards the central longitudinal direction of the article. In a further embodiment, the liquid permeable first topsheet layer includes multiple, similarly shaped uninterrupted aperture openings of at least two different sizes through the layer entire thickness. In yet another alternative embodiment, the multiple aperture openings are arranged in total, to resemble an oval shape. In still another alternative embodiment, the multiple aperture openings are aligned along the central longitudinal direction. In yet another embodiment, the liquid permeable first topsheet layer includes a centrally located, single oval or circular shaped, uninterrupted aperture opening through the entire thickness of the layer.

In another embodiment, the liquid permeable first topsheet layer includes a user-facing, skin contacting surface and an opposing garment-facing surface, with the garment-facing surface having a non-absorbent, fluid transfer layer attached thereto, along the entire fluid transfer layer dimensions (length and width). In yet another alternative embodiment, the fluid transfer layer includes at least one aligned aperture opening through its entire thickness, that is aligned along the absorbent article depth direction with the aperture opening or openings of the first topsheet layer, alternatively, is of the same shape and size as the at least one uninterrupted aperture opening of the liquid permeable first topsheet layer.

In still another alternative embodiment, the fluid transfer layer includes at least one aperture opening through its entire thickness, that is either larger in at least one dimension than the uninterrupted aperture opening of the liquid permeable first topsheet layer, or smaller in dimension, but which does not completely block the liquid communication passageway to the second topsheet layer, or the visualization of the second topsheet through the liquid permeable first topsheet layer. In another alternative embodiment, the one aligned aperture opening of the transfer layer is of a single oval or circular shape. In still a further alternative embodiment, the transverse direction width dimension of the fluid transfer layer is narrower than the transverse direction dimension of the liquid permeable first topsheet layer. In yet another alternative embodiment, the fluid transfer layer is visually distinguishable from the liquid permeable first topsheet layer, such as to accentuate the size or shape of the uninterrupted aperture opening to the article user. Such visual distinction may be by a color or texture difference between the first topsheet layer and transfer layer, that is visible to the user through the first topsheet layer. In another alternative embodiment, the color of the liquid permeable first topsheet layer may be different than that of the second topsheet layer so as to emphasize the presence of the aperture opening in the first topsheet layer, by creating a background color contrast.

In yet another alternative embodiment, the absorbent article includes an additional apertured, liquid permeable topsheet layer situated between the liquid permeable first and second topsheet layers, the additional apertured liquid permeable topsheet layer being attached (either directly or indirectly through the noted transfer layer) to the liquid permeable first topsheet layer. Such additional apertured liquid permeable topsheet layer may be attached to the garment-facing surface of the liquid permeable first topsheet layer, or alternatively, to the garment-facing surface of a transfer layer, which is itself attached to the garment-facing surface of the liquid permeable first topsheet layer. Such layers would be capable of separating as a unit, from the subjacent liquid permeable second topsheet layer to form a gap between them during prolonged article use. Alternatively, such additional apertured liquid permeable topsheet layer is attached to both the liquid permeable first topsheet layer and the transfer layer. Still in a further alternative embodiment, such additional apertured liquid permeable topsheet layer is transparent or almost transparent, so as to continue to allow the visualization of the liquid permeable second topsheet layer (or a layer beneath the second topsheet layer) through it when viewed from the user-facing surface of the liquid permeable first topsheet layer (and the uninterrupted aperture opening). In another alternative embodiment, the additional apertured, liquid permeable topsheet layer includes multiple shaped and sized apertures, such apertures allowing the unimpeded passage of fluid/exudate to the second topsheet layer from the user. In a further alternative embodiment, at least some of the apertures of the additional apertured, liquid permeable topsheet layer are smaller in dimension than the uninterrupted aperture opening(s) of the liquid permeable first topsheet layer and/or transfer layer (if present). In a further alternative embodiment, such additional apertured, liquid permeable topsheet layer is an apertured film sheet. In yet another alternative embodiment, such additional apertured, liquid permeable topsheet layer includes regularly spaced apertures extending across the uninterrupted aperture opening of the liquid permeable first topsheet layer.

In still another alternative embodiment, the liquid permeable first topsheet layer includes opposing lateral, folded-over side edges, such as Z-folds, adjacent each of its first topsheet layer opposing lateral side edges for attachment to and extension from the liquid permeable second topsheet layer, such as for example, from the second topsheet layer opposing lateral side edges or a position inward of the second topsheet layer opposing lateral side edges. Therefore such liquid permeable first topsheet layer may take on the appearance of a floating topsheet layer above the second topsheet layer. Such upper topsheet layer can therefore be present in a relatively flatter configuration with only opposing lateral side edges anchored directly to an underlying second topsheet layer, or alternatively, in a more exaggerated elevated version with Z-folded over lateral side edges, which are also still anchored directly to the underlying second topsheet layer, but which provide enhanced height as a result of the lateral side edge Z-fold structures and the bend line. In another alternative embodiment, the liquid permeable first topsheet layer is attached at attachment zones to the liquid permeable second topsheet layer adjacent its second topsheet layer opposing lateral side edges, through at least one bonding method selected from the group consisting of adhesive, ultrasonic, and thermal bonding methods. Desirably in one embodiment, such first topsheet layer demonstrates a rigidity as a result of multiple attached layers, to assist it in maintaining a generally convex configuration (along the transverse direction) above the second topsheet layer.

In still a further alternative embodiment, the liquid permeable second topsheet layer further includes a center topsheet layer portion, and side topsheet layer portions adjacent the absorbent article opposing lateral side edges, and the liquid permeable first topsheet layer includes first topsheet layer opposing lateral side edges that are attached to the liquid permeable second topsheet layer either at the side topsheet layer portions, at the center topsheet portion, or a combination of both the side topsheet and center topsheet layer portions. In a further alternative embodiment, such side topsheet layer portions have inside edges, and the liquid permeable first topsheet layer is attached via attachment zones to the center topsheet portion at a location between the inside edges of the side topsheet layer portions. In another alternative embodiment, the liquid permeable first topsheet layer and the liquid permeable second topsheet layer are of the same dimensions along the absorbent article longitudinal and transverse directions. In another embodiment, the liquid permeable first topsheet layer includes a liquid permeable first topsheet layer longitudinal and transverse direction, the liquid permeable second topsheet layer includes a liquid permeable second topsheet layer longitudinal and transverse direction, and the liquid permeable first topsheet layer differs in dimension from the liquid permeable second topsheet layer at least along either the transverse or longitudinal direction. In one embodiment, the liquid permeable first topsheet layer is smaller in overall dimension than the liquid permeable second topsheet layer, and alternatively, is centrally located on/above the liquid permeable second topsheet layer when viewed from the article Z direction. In a further alternative embodiment, the liquid permeable first topsheet layer is smaller in overall dimension than the liquid permeable second topsheet layer, and while being located on the liquid permeable second topsheet layer along the central longitudinal direction, is located more towards one of the longitudinal ends of the absorbent article than the other longitudinal end. In yet a further alternative embodiment, the liquid permeable first topsheet layer differs in dimension from the liquid permeable second topsheet layer along both transverse and longitudinal directions of the absorbent article. In another alternative embodiment, the liquid permeable first topsheet layer differs in dimension from the liquid permeable second topsheet layer along only one of the transverse or longitudinal directions of the absorbent article.

In still another embodiment, the liquid permeable first topsheet layer is shorter along the absorbent article longitudinal direction than said liquid permeable second topsheet layer. In a further embodiment, the absorbent article includes an initial, fluid deposition region along the article user-facing, skin contacting surface, and the liquid permeable first topsheet layer is situated in the initial, fluid deposition region. In still another embodiment, the absorbent article includes a central longitudinal direction or axis, and the at least one uninterrupted aperture opening is symmetrically positioned along the absorbent article central longitudinal direction or axis. In a further alternative embodiment, such aperture opening is sized to fit about a user's perineal or alternatively vaginal area.

In still another embodiment, an apertured film layer is subjacent and connected to a fluid transfer layer in the absorbent article depth direction, the apertured film layer being positioned between the fluid transfer layer and the liquid permeable second topsheet layer, but not connected to the liquid permeable second topsheet layer.

In yet another alternative embodiment, the liquid permeable first topsheet layer is hydrophobic or generally hydrophobic, being fashioned from inherently hydrophobic materials or being made so through surface treatments or polymer blends. In yet another alternative embodiment, the liquid permeable first topsheet layer is generally hydrophobic and the liquid permeable second topsheet layer is generally hydrophilic.

In another alternative embodiment of the invention, a further fluid directing or transfer layer is positioned between the liquid permeable second topsheet layer and the one or more absorbent core layers. The further fluid directing or transfer layer itself includes an aperture opening through its entire thickness, which is both sized and shaped to match the size and shape of the uninterrupted aperture opening of the liquid permeable first topsheet layer, and alternatively, if present, also the openings of either the transfer layer and/or additional topsheet layer that may be attached to the first topsheet layer. In one embodiment, this aperture is also aligned with such uninterrupted aperture opening of the first topsheet layer when viewed along the article L, T, and Z directions, and alternatively, if present, the opening in the transfer layer. Other features and aspects of the present invention are described in more detail below.

BRIEF DESCRIPTION OF THE DRAWINGS

A full and enabling disclosure of the present invention is set forth more particularly in the remainder of the specification, including reference to the accompanying figures, in which.

DEFINITIONS

Figure 1:
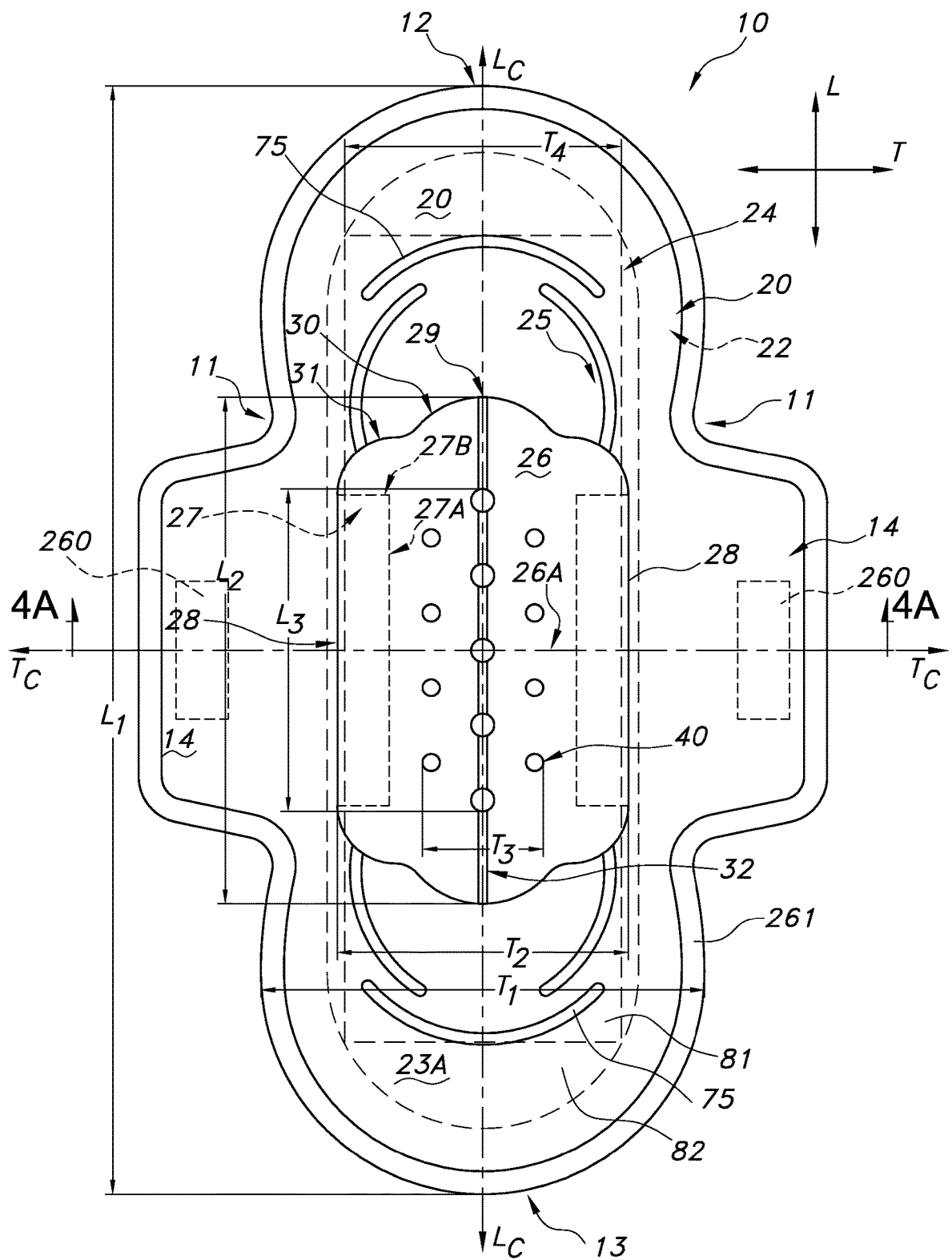
FIG. 1 illustrates a top plan view of a feminine care absorbent personal care article in accordance with the invention, in the form of a sanitary pad.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, hydroentangling, and bonded carded web processes (such as through-air bonded carded webs or TABCW).

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Butin, et al., which is incorporated herein in its entirety by reference thereto. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto. Spunbond fibers are generally not tacky when they are deposited onto a collecting surface. Spunbond fibers may sometimes have diameters less than about 40 microns, such as between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 5,284,703 to Everhart, et al., and U.S. Pat. No. 5,350,624 to Georger, et al., each of which are incorporated herein in their entirety by reference thereto.

As used herein, the term "storage component" refers to an absorbent article layer which primary function is designed to ultimately store body exudate in the form of liquid/fluid waste. That is, such storage component is an absorbent layer designed to retain aqueous-based liquid/fluid, after the liquid has been received into an absorbent article through a topsheet layer, and optionally through liquid handling layers such as surge, transfer, and distribution layers. Such storage component layer may include for example, superabsorbent materials (or SAPs) as are known in the absorbent article art, but generally includes all or primarily hydrophilic materials such as cellulosic wadding, or other cellulosic-based materials, porous foams, or other hydrophilic liquid retaining materials for example. A liquid/fluid storage component is to be distinguished from a topsheet layer, or an intermediate liquid/fluid handling layer such as a surge, transfer, distribution, or directing layer, that are each designed as "pass-through" layers to perform a function on liquid as it passes from an initial liquid/fluid receiving layer to the fluid storage component. Pass-through layers pass liquid through the layer as it travels to its ultimate storage destination. Examples of various functions of a pass-through layer may be to slow down liquid flow, to spread the flow of liquid along multiple directions on an adjacent layer, to channel fluid quickly to a lower layer within an article, or to perform a specific separation operation or treatment on the liquid, as it passes through the layer to a storage layer. An initial liquid/fluid receiving layer (ie topsheet layer) of an absorbent article having at least a topsheet layer, absorbent core layer, and backsheet layer (i.e. at least the first, user-facing topsheet layer of a multilayered absorbent article in the article depth direction), shall not be considered a "storage component" for the purposes of this application. The incidental presence of initially received liquid/fluid on a topsheet layer, or the rewet of such topsheet layer, shall not for the purposes of this application, constitute ultimate liquid storage. Desirably, in one embodiment such topsheet layer retains little to no liquid. In an alternative embodiment, such topsheet and any directly attached layer thereto that is attached across substantially most (greater than 50%) of the topsheet garment-facing underside surface along the topsheet layer length, retains little to no liquid. Desirably, in a further embodiment, such topsheet layer and any optional, directly attached layer are manufactured entirely from hydrophobic materials. Desirably in one embodiment, such topsheet layer does not include any other layer attached to it, except at its opposing lateral side edges, with such other attached layer being a secondary topsheet layer.

As used herein, the term "hydrophobic" shall refer to a material having a contact angle of water in air of at least 90 degrees. The terms "hydrophilic" and "wettable" are used interchangeably to refer to a material having a contact angle of water in air of less than 90 degrees. The phrase "more hydrophilic" shall refer to a material having a relatively lower contact angle. The phrase "more hydrophobic" shall refer to a material having a relatively higher contact angle. Hydrophobicity and hydrophilicity can both be the result of the inherent properties of the composition making up a material. For example, polyolefinic and/or elastomeric polymers are typically hydrophobic, while cellulosic materials are typically hydrophilic. Alternatively, such properties may be the result of coatings that have been added to base substrates.

For the purposes of this application, contact angle measurements can be measured using a Cahn SFA-222 Surface Force Analyzer System, or a substantially equivalent system. Contact angles can be determined as set forth in Neumann, A. W., and R. J. Good, "Techniques of Measuring Contact Angles," Chapter 2, Surface and Colloid Science—Experimental Methods, Vol. 11, edited by R. J. Good and R. R. Stromberg, Plenum Press, 1979, pp. 31-91, which is hereby incorporated by reference in a manner that is consistent herewith. For coated substrates, contact angle measurement may be made in accordance with ASTM D-7334, titled "Standard Practice for Surface Wettability of Coatings, Substrates and Pigments by Advancing Contact Angle Measurement". Such advancing contact angle measurement is preferred unless otherwise noted. Examples of hydrophobic surface treatments that may be used to coat particular topsheet layers include those described in United States patent publication 2013/0197462 to Abuto et al., which is hereby incorporated by reference thereto for purposes not inconsistent herewith.

As used herein, the term "liquid permeable" shall refer to a material which is porous and which is water permeable due to the flow of water and other aqueous liquid or fluid through the pores. The pores are large enough and frequent enough to permit leakage and flow of liquid water. "Liquid impermeable" shall refer to a material that does not allow water or aqueous liquid/fluid to pass through it under ordinary use conditions.

The term "uninterrupted" shall refer to an opening that extends through the entire thickness of a layer, such that liquid can flow directly through the layer to a lower layer without contacting any intermediate layer, and the lower layer can also be visually seen through the opening or a portion thereof, without being completely visually obscured by an intermediate layer.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not illustrated in most figures except where additional placement emphasis is desired, it should be understood that traditional article construction adhesive (or other bonding technology) is to be used to fasten the various layers of the described articles together. Such construction adhesive or other bonding technology is desirably placed or practiced so as not to interfere with the flow of liquid waste through the article. Other bonding techniques include for example, ultrasonic, pressure, and thermal bonding.

Generally speaking, the absorbent personal care articles of the present invention are ideally suitable for use as hygiene articles in the feminine and adult care product categories. Such articles include for example, feminine sanitary pads and liners, and adult care garment inserts, pads, and liners. Such articles will include a user-facing surface or skin-contacting topsheet layer, made up of a liquid permeable first topsheet layer, which is positioned over a liquid permeable second topsheet layer, and which liquid permeable first topsheet layer is partially separable from the liquid permeable second topsheet layer between two lateral attachment zones. In actuality, both the liquid permeable first topsheet layer and the liquid permeable second topsheet layer may be user-facing, skin-contacting layers depending on the particular embodiment. In some embodiments, the liquid permeable second topsheet layer may contact the skin of a user around the peripheral edges of the desirably smaller dimensioned liquid permeable first topsheet layer. The liquid permeable second topsheet layer may also contact the skin of a user through a centrally positioned aperture opening (or multiple proximate openings) defined by an interior edge or edges of the liquid permeable first topsheet layer. The uninterrupted aperture opening(s) extend through the entire thickness of the first topsheet layer. It should be understood that the liquid permeable first topsheet layer material, is liquid permeable regardless of the presence of the aperture opening.

The liquid permeable first topsheet layer acts to physically separate a skin-contacting layer from the rest of the pad by forming a changeable spatial gap therebetween, and is partially separable from the liquid permeable second topsheet layer along the article transverse direction, between the two laterally opposed attachment zones. Such liquid permeable first topsheet layer may include a similar overall dimension as the liquid permeable second topsheet layer, or may alternatively, be of smaller overall dimension than the liquid permeable second topsheet layer such that both first and second topsheet layers make physical contact with a user's skin at some time during article use. While such liquid permeable first topsheet layer maintains close proximity and contact with the user's skin, it also allows for a void space to be sporadically formed between it and much of the rest of the pad in use (and specifically the liquid permeable second topsheet layer), hence keeping moisture that may be trapped in underlying absorbent layers from continuously traveling back through the pad to the user's skin during prolonged article use. Such partially separable skin-contacting layer assists in maintaining dryness at the skin level and reducing rewet sensations. While the liquid permeable first topsheet layer is only attached at its opposing lateral side edges to the underlying pad, specifically at select locations along the liquid permeable second topsheet layer, the liquid permeable second topsheet layer in contrast, is attached to the pad absorbent structure along much of the pad length and width dimensions. As a result of these different levels of connection, at certain times during article use the two topsheet layers make significant contact with each other along their dimensions, to allow for transfer of liquid from the first topsheet layer to the second topsheet layer. At other times, the two topsheet layers are substantially separated from one another as the user moves about during his/her daily activities.

Since the aperture opening(s) of the first topsheet layer are in one embodiment, designed to be dimensioned to closely surround a user's perineal or vaginal region, exuded liquid can flow directly to a subjacent layer through the first topsheet layer opening(s), thereby maintaining dryness along the first topsheet layer, user-facing surface. Under downward pressure from the body, the two topsheet layers may be in contact. However, while a user moves, gaps form between the two topsheet layers (which are capable of separating along most of their dimensions and especially along their length). Such gaps keep moisture within the pad from resurfacing to the skin through the first topsheet layer and also allow for air circulation between the two topsheet layers.

The liquid permeable first topsheet layer includes opposing free longitudinal ends, and longitudinally directed side edges (or opposing lateral side edges) which side edges are attached to the liquid permeable second topsheet layer at or adjacent these opposing lateral side edges of the first topsheet layer, and desirably also, at or adjacent the opposing lateral side edges of the pad. In embodiments in which the dimensions of the liquid permeable first topsheet layer are smaller than the dimensions of the liquid permeable second topsheet layer, the two may be connected either inward from the opposing lateral side edges of the second topsheet layer or alternatively, the opposing lateral side edges of the pad. A continuous longitudinally directed passageway or void space may be formed during use, between the two liquid permeable topsheet layers upon the partial or total lifting of the liquid permeable first topsheet layer away from the liquid permeable second topsheet layer.

At least one centrally positioned aperture opening is defined by the liquid permeable first topsheet layer, and the opening extends through the layer's entire thickness to the liquid permeable second topsheet layer uninterrupted by any intermediate material (such as from any intermediate fluid transfer or surge layer). Essentially the opening extends completely there-through the first topsheet layer and any optionally connected intermediate layers, and directly to the user-facing surface of the liquid permeable second topsheet layer, thereby allowing liquid to directly travel through the first topsheet layer to the surface of the second topsheet layer, and also for the viewing of the second topsheet layer through the first topsheet layer. Any intermediate liquid/fluid transfer layer that may be bonded to the underside (garment-facing side) of the liquid permeable first topsheet layer if present, does not include a liquid storage component. In such embodiments, such bonded intermediate layer would also include an aperture opening extending entirely through the thickness of that layer and aligned with the aperture opening of the liquid permeable first topsheet layer, or a portion thereof such that a first topsheet layer opening extends uninterrupted to the liquid permeable second topsheet layer user-facing surface. Desirably, such intermediate layer opening extends the full dimensions of the liquid permeable first topsheet layer opening and is aligned therewith. The opening or aligned openings (as the case may be) allow for direct liquid communication from the point of liquid entry on the pad to the second topsheet layer user-facing surface. Such opening(s) also allows for the direct visualization of the second topsheet layer through the first topsheet layer.

In desirable embodiments, openings in any intermediate liquid transfer layer are all at least partially aligned with at least one aperture opening of the liquid permeable first topsheet layer, such that there is no interference with liquid flow that passes through the liquid permeable first topsheet layer to the liquid permeable second topsheet layer. In one embodiment, the liquid permeable second topsheet layer can be directly seen through the aperture opening(s) of the liquid permeable first topsheet layer (through the opening full dimensions) when viewed from the user-facing surface of the first topsheet layer. The liquid permeable first topsheet layer includes an oval or circular aperture opening in one embodiment, that has been sized and shaped to encompass the user's perineal region, and desirably a woman's vaginal region. In an alternative embodiment, multiple proximate openings in the first topsheet layer are situated in a central liquid acquisition zone on the pad. The aperture openings in the first topsheet layer (and any optional intermediate layers and/or lower internal article layers) are macro-openings, in that they are typically formed by cut-out, punching or aperturing processes for openings of a relatively large dimension. Such openings are to be distinguished from the relatively smaller openings of liquid permeable layers formed from interstitial spaces between adjacent nonwoven fibers, or those found in microapertured films, such as those formed by vacuum aperturing processes.

The liquid permeable first topsheet layer is desirably capable of bending upward, such as in an inverted "V" shape, along a bend or fold line so that it preferentially separates from layer(s) subjacent to it in use. Such bend or fold line is desirably created by an embossment feature on one or both sides/surfaces of the liquid permeable first topsheet layer, desirably along the article central longitudinal axis/direction. The liquid permeable first topsheet layer is desirably shaped and sized overall, to be positioned beneath the liquid deposition region of a user (or perineal region, alternatively vaginal region) and over the initial liquid deposition region of the absorbent article. The initial liquid deposition region of the absorbent article is desirably the central region of the article, located along the central longitudinal axis or direction of the article, and alternatively, also along a central transverse axis or direction if present. Alternatively, such region may also be positioned in a forward location on such an article, especially if such article is intended for overnight use, and the article is of an extended length shape or of an asymmetrical shape. Typically such overnight absorbent article would be of an extended asymmetric shape having a narrower transverse direction width at one longitudinal end and a wider transverse direction width at the opposing end. In such an article, the liquid permeable first topsheet layer is desirably placed closer to the narrower width end than the wider width end, and alternatively, adjacent any article wings if present.

The liquid permeable first topsheet layer is also desirably more hydrophobic than the liquid permeable second topsheet layer. In other words, the liquid permeable second topsheet layer is desirably more hydrophilic than the liquid permeable first topsheet layer.

In use, the absorbent article provides for two separable topsheet layers, which separate from one another along the article depth direction, and which also physically separate a user from soiling that may be contained in the absorbent article. This physical separation occurs without storing liquid waste immediately adjacent the user-facing surface of the first topsheet layer, located over the initial fluid deposition region of the article. For example, in one embodiment, such liquid permeable first topsheet layer is a single layer of material (or alternatively, a multiple layer topsheet) that is attached as noted to the liquid permeable second topsheet layer only along its opposing lateral side edges, without any other layer there-between. Desirably, such liquid permeable first tospheet sheet layer is hydrophobic, and such liquid permeable second topsheet layer is hydrophilic. In certain embodiments, additional apertured liquid permeable layers can be attached either directly or indirectly to the underside of the liquid permeable first topsheet layer (and above the liquid permeable second topsheet layer). In such a situation as will later be described, the liquid permeable first topsheet layer may optionally include an attached fluid transfer layer, an attached additional apertured liquid permeable topsheet layer, or a combination of both, which attached layers separate or raise up as a unit, from the underlying liquid permeable second topsheet layer during article use. Such separation creates a void space between the layers.

As can be specifically seen in FIG. 1, a top plan view of a generally planar absorbent personal care article in the form of a feminine care sanitary pad 10 is illustrated. A feminine sanitary pad is provided for the purposes of illustration only, and it should be appreciated that a variety of absorbent articles can also benefit from the present invention, including for example, feminine hygiene panty liners and various adult care absorbent articles. The sanitary pad is illustrated in a generally planar and unfolded state for ease of viewing. The sanitary pad 10 includes a longitudinal direction (or axis) L, a transverse direction (or axis)T, and a depth direction (or axis) Z (as seen for example in FIG. 3B). The sanitary pad 10 also includes an optional central longitudinal direction (or axis) $L_c$. Some embodiments may also include a central transverse direction (or axis) Tc. The sanitary pad includes longitudinally directed opposing side edges (or article opposing lateral side edges) 11 and opposing longitudinal (direction) ends 12, 13. Optional extensions 14 may protrude from the article opposing lateral side edges 11. Such extensions 14 will be described further herein, but are also known as either wings or tabs in the feminine care art. The sanitary pad 10 includes a liquid permeable first topsheet layer 26 having one or more aperture openings 40, 60 (FIG. 2G), a liquid permeable second topsheet layer 20 (also known as second topsheet layer), and a liquid impermeable backsheet layer 22, which second topsheet layer 20 and backsheet layer 22 together sandwich an absorbent core layer 24 structure seen in phantom. The aperture openings 40 (FIG. 1), 60 (FIG. 2G) are uninterrupted, thereby allowing for direct fluid communication of exudate from the user to the second topsheet layer 20 user-facing surface, and the viewing of the second topsheet layer 20 through the first topsheet layer 26, without relying on the transparency of the first topsheet layer material. The absorbent core layer 24 is the ultimate, liquid/fluid storage component of the article. Generally, such absorbent core layer structure 24 may include one or multiple layers 81, 82. Additional liquid/fluid handling layers 80, such as liquid surge, fluid delay, and fluid transfer layers may be positioned in the article, such as between the absorbent core layer structure 24 and the second topsheet layer 20 (as seen for example in FIG. 4D). Such fluid handling layer 80 may itself define an aperture opening 83 (FIG. 4D) which creates a direct liquid communication passageway to the subjacent absorbent core layer 24 from the second topsheet layer 20. If present, the aligned openings of the fluid handling layer 80 and the liquid permeable first topsheet layer 40, 60 may act to create a funnel-like structure to quickly direct liquid to the absorbent core layer (storage component) 24 of the absorbent article. The quick passage is hardly impacted by the hydrophilic second topsheet layer 20. As seen for example in FIGS. 3D, 4A,and 4B the liquid permeable second topsheet layer 20 includes a liquid permeable second topsheet layer user-facing surface 23A and a garment-facing surface 23B. Optional embossment features (that is, layer indentations in the form of lateral side patterns 25 or end patterns 75) may be present through one or more layers in the sanitary pad 10 to assist with liquid flow or pad stability, or to provide aesthetic ornamentation. While such embossments are shown as rounded arcs, it should be appreciated that any number of known embossment shapes and patterns may be used on such a sanitary pad 10, formed by known embossment techniques.

Figure 3A:
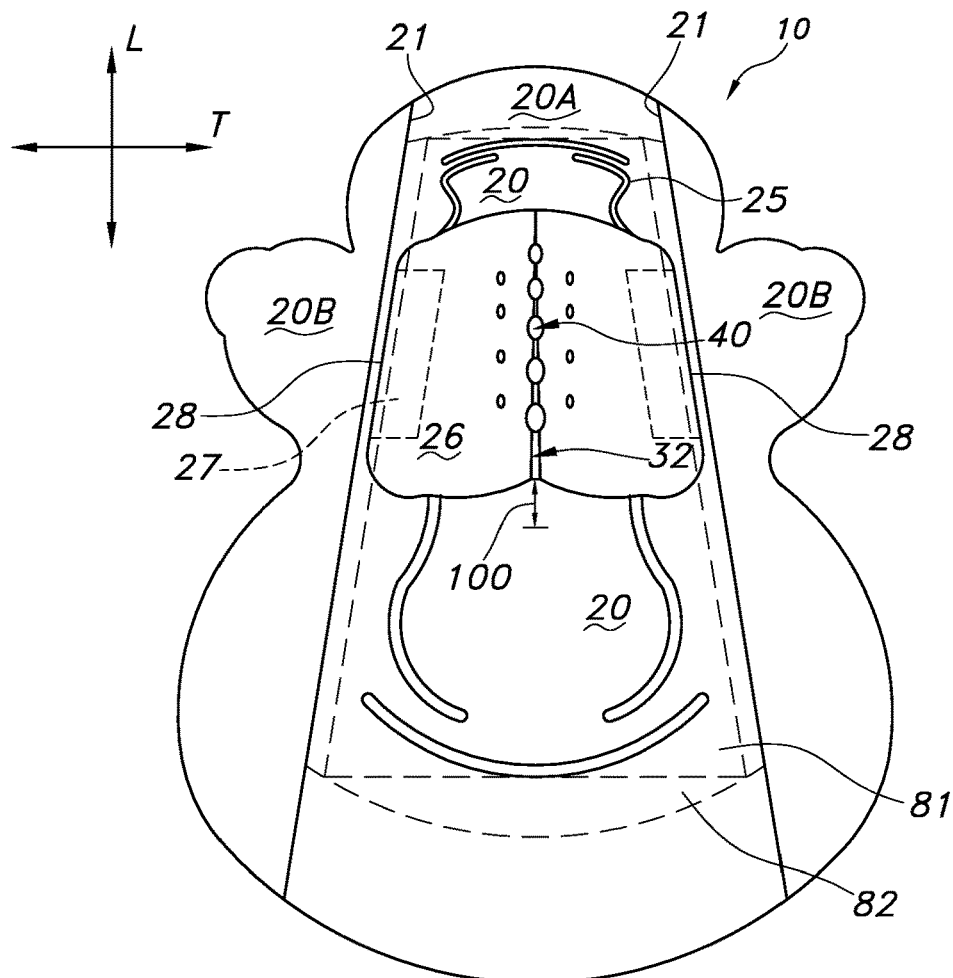
FIG. 3A illustrates a top surface perspective view of another alternative embodiment of a sanitary pad in accordance with the invention in which an asymmetrical pad is shown.
Figure 3B:
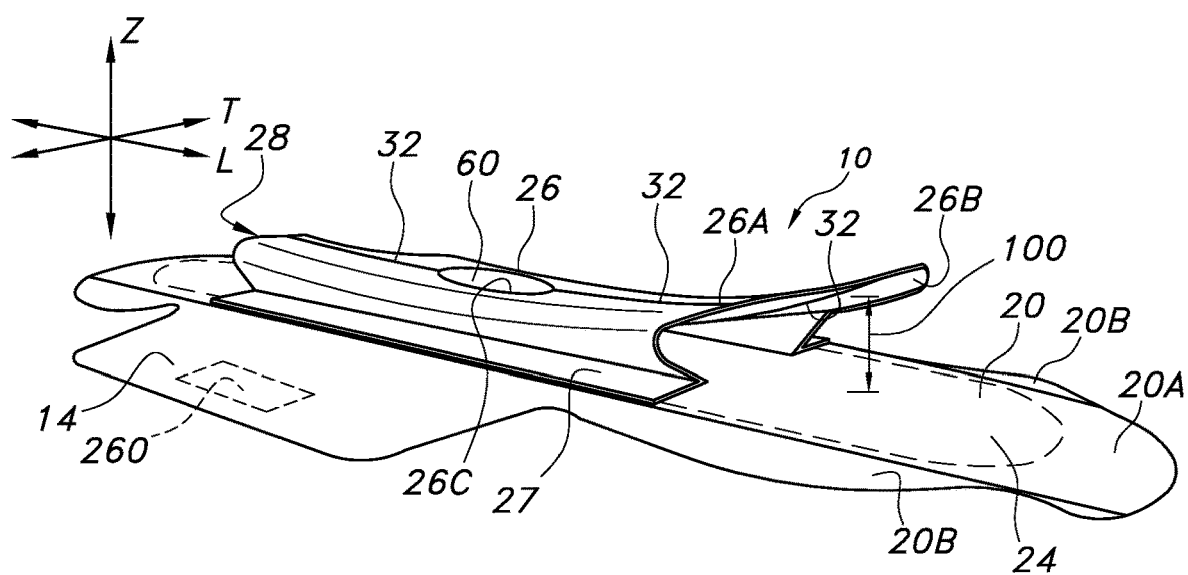
FIG. 3B illustrates a side perspective view of another alternative embodiment of a sanitary pad in accordance with the invention.

The liquid permeable first topsheet layer 26 (that is, the partially separable topsheet layer also known as the first topsheet layer) is situated above the liquid permeable second topsheet layer 20 in the article Z direction (as seen in FIG. 3B). The liquid permeable first topsheet layer 26 is identified as such, as it is the uppermost layer in the article Z direction and will always make contact with the skin of the article user. As seen in FIG. 1, the liquid permeable first topsheet layer 26 is in one embodiment, of overall dimensions that are narrower and shorter than the underlying liquid permeable second topsheet layer 20, and is situated in a central liquid deposition region of the pad (such as adjacent the pad wings (if present), and along the central longitudinal direction, and optionally along the central transverse direction). Such narrower and shorter dimensions are helpful if the pad is to be folded in three sections along two fold lines along the transverse direction (not shown). Desirably if present, such fold lines would not cross the liquid permeable first topsheet layer 26.

Figure 2A:
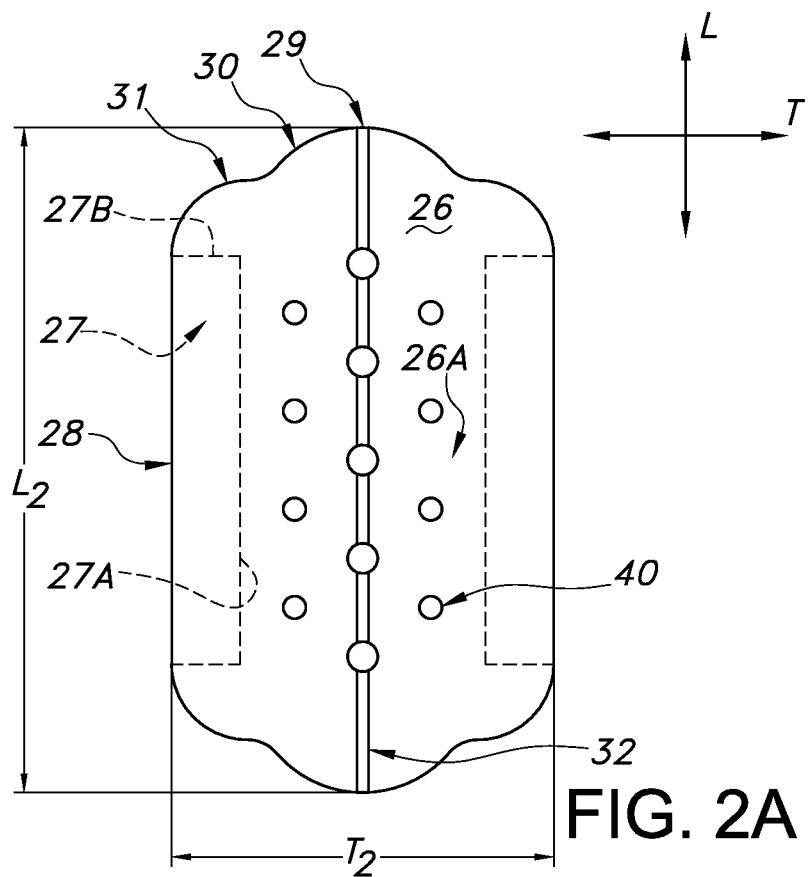
FIG. 2A illustrates a top plan view of the user-facing surface of only the partially separable liquid permeable first topsheet layer of the sanitary pad of FIG. 1.
Figure 2B:
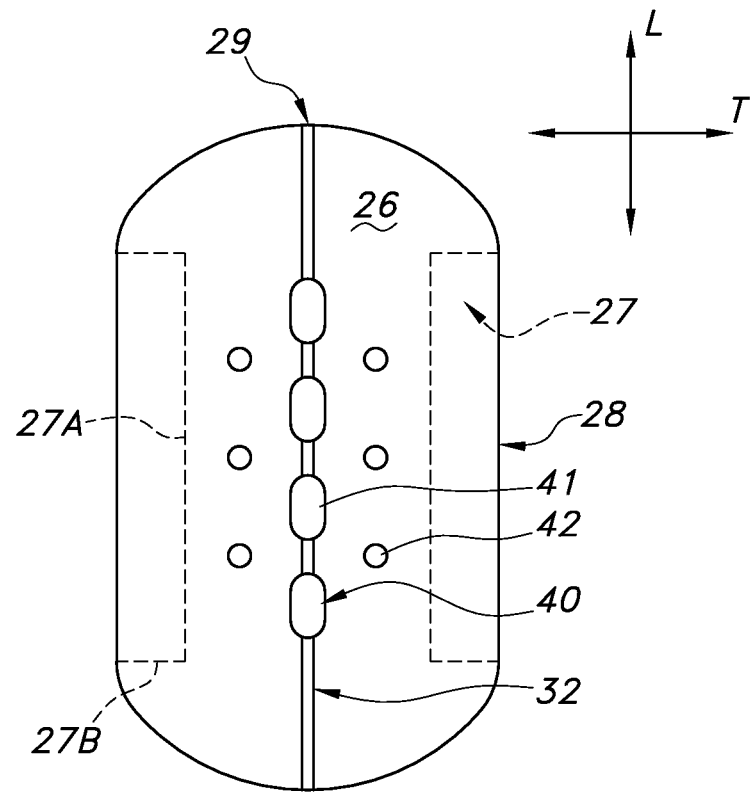
FIG. 2B illustrates a top plan view of the user-facing surface of an alternative embodiment of only the partially separable liquid permeable first topsheet layer of the sanitary pad of FIG. 1.
Figure 2C:
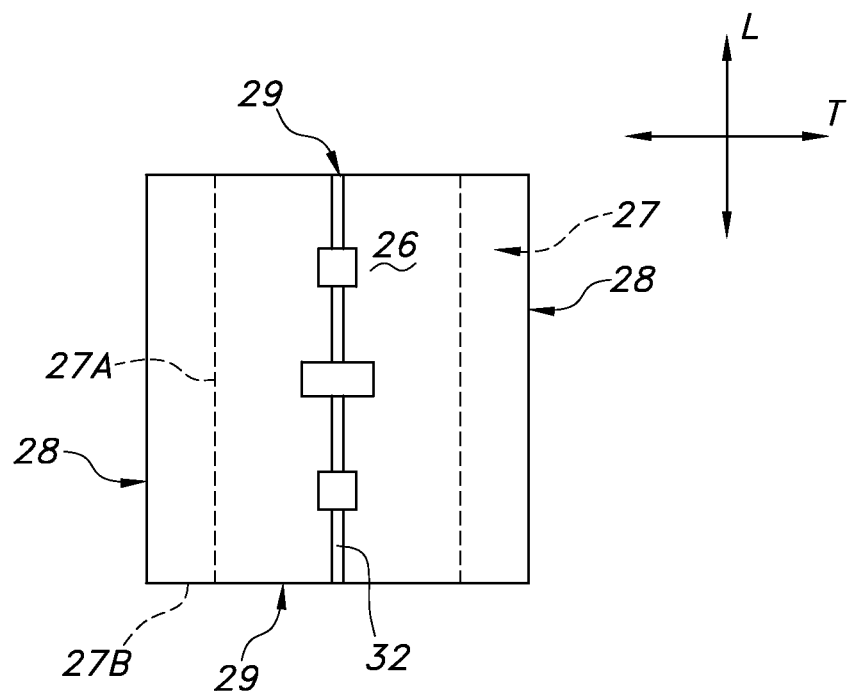
FIG. 2C illustrates a top plan view of the user-facing surface of another alternative embodiment of only the partially separable liquid permeable first topsheet layer of the sanitary pad of FIG. 1.

The liquid permeable first topsheet layer 26 includes liquid permeable first topsheet layer, opposing lateral side edges 28 (along the transverse direction), and liquid permeable first topsheet layer opposing longitudinal ends 29. Such end dimensions may be uniform in length, such as straight edges as shown in FIG. 2C, or alternatively as shown in FIG. 1, may include multiple curved features 30, 31 such that the opposing longitudinal ends do not have uniform length dimensions along the transverse direction. The liquid permeable first topsheet layer 26 includes a user-facing surface 26A and a garment-facing (or absorbent core layer-facing) surface 26B as seen in FIG. 3B. The liquid permeable first topsheet layer 26 opposing lateral side edges 28 may be anchored to the liquid permeable second topsheet layer 20 either directly at or adjacent to such opposing lateral side edges (as seen in FIGS. 3C, 3D, 4B, 4E), or connected via folded-under edge portions 27, having folded-under longitudinally directed edges 27A, and folded-under transversely directed edges 27B. Such folded-under features form laterally opposing Z-like folds between the topsheet layers. Such attachments at attachment zones 70, may be by any known traditional bonding techniques, such as for example by ultrasonic, adhesive, thermal, stitch or a combination of such bonding methods. The bonding occurs in the opposing attachment zones 70 (as seen in FIG. 2F) either directly between the garment-facing surface of the first topsheet layer and the user-facing surface of the second topsheet layer, or alternatively, between the garment-facing surface of the folded-under edges and the user-facing surface of the second topsheet layer. The length of the attachment zones or folded-under longitudinally directed edges 27A, may extend the full or partial length of the opposing lateral side edges 28. For example, in one embodiment, the attachment zones may extend greater than 50% of the length of each of the first topsheet layer opposing lateral side edges 28, alternatively, greater than 80% of the length of the opposing lateral side edges 28, alternatively, greater than 90% of the length of the opposing lateral side edges 28, such as by use of a line of adhesive, thermal, or ultrasonic bonding technique. In one embodiment, such attachment zone is created by a line of adhesive along each opposing lateral side edge 28, with such line of adhesive having a transverse direction width of between about 2 mm and 18 mm, alternatively between about 4 mm and 9 mm. In one embodiment, the percent of first topsheet layer 26 surface area (garment-facing surface 26B) that is bonded to the second topsheet layer user-facing surface at such attachment zones 70, is less than 50%, alternatively less than 70%, alternatively, less than 90%. The folded-under transversely directed edges 27B (and attachment zones) are desirably not substantial in width, relative to the width of the first topsheet layer along the article transverse direction, such that they do not interfere with liquid flow through the first topsheet layer in the Z direction, especially in the central region of the pad. For example, in one embodiment, such folded-under transversely directed edges 27B are between about 3 mm and 20 mm in width, alternatively between about 5 and 10 mm in width. The longitudinal dimensions of the folded-under edges 27A may in one embodiment be between about 50 mm and 180 mm, alternatively between about 60 mm and 120 mm. In either situation, the connection or opposing attachment zones, each allow for the liquid permeable first topsheet layer 26 to be elevated above the liquid permeable second topsheet layer 20 during use, in response to pad compression and/or user movements. While the folded-under embodiment is shown as a single Z-fold, that is one each for the two opposing folds in FIG. 4A, it may also include more vertical folds in the Z-direction, such as for example two or three folds along each opposing lateral side edge (not shown).

Figure 4A:
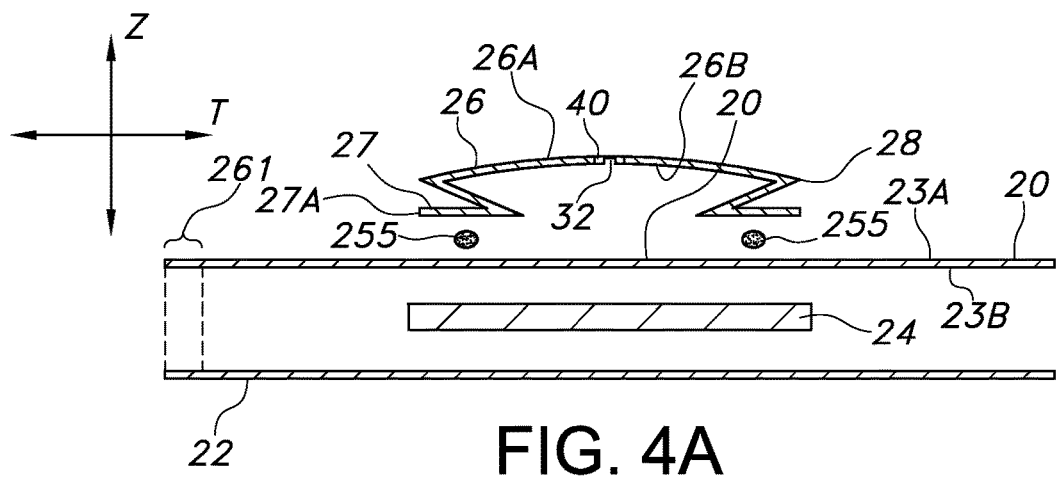
FIG. 4A illustrates an exploded, cross-sectional view of the sanitary pad of FIG. 1, taken along line 4A-4A.
Figure 4B:
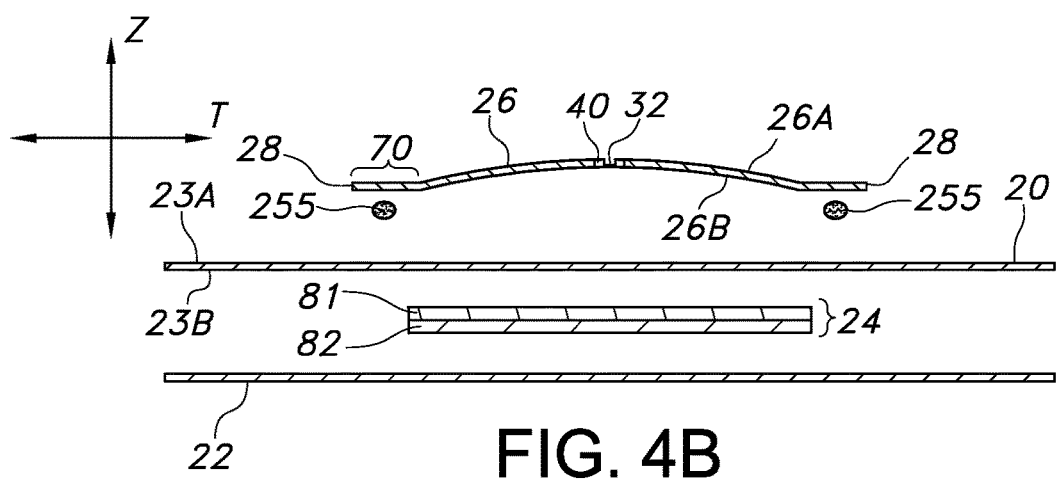
FIG. 4B illustrates an exploded, cross-sectional view of the sanitary pad of FIG. 2F, taken along line 4B-4B.
Figure 4C:
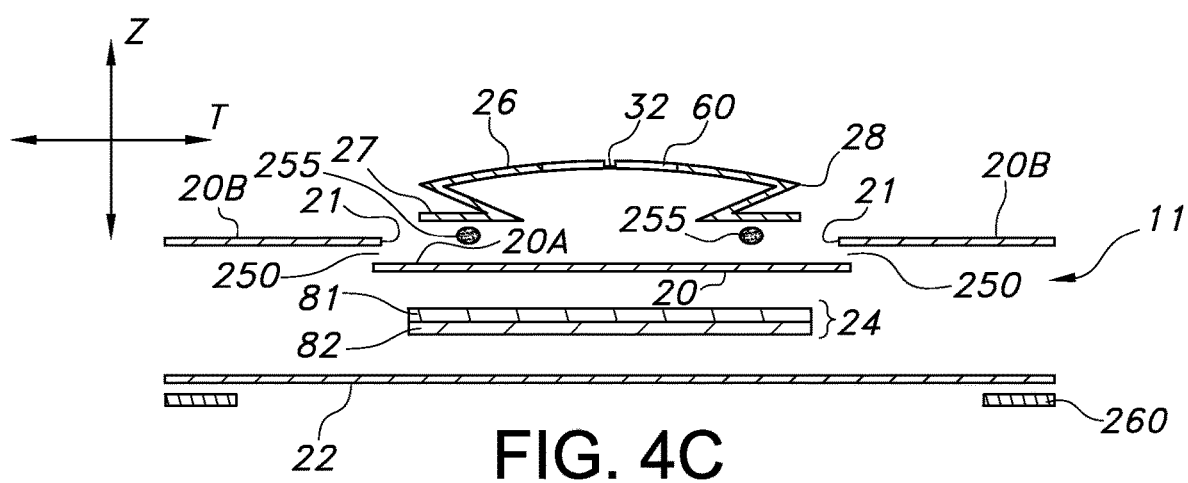
FIG. 4C illustrates an exploded, cross-sectional view of the sanitary pad of FIG. 2G, taken along line 4C-4C.
Figure 4D:
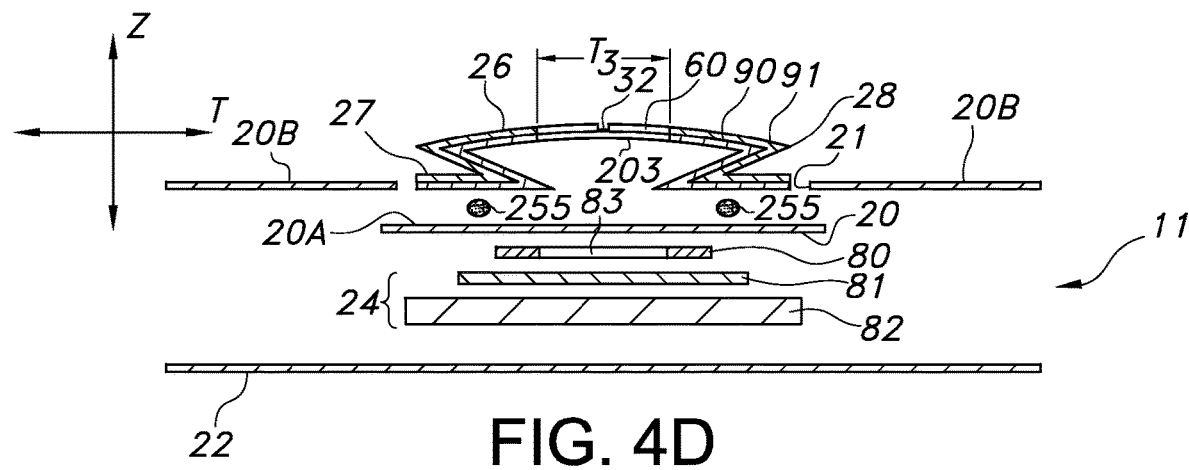
FIG. 4D illustrates an exploded, cross-sectional view of the sanitary pad of FIG. 2H, taken along line 4D-4D.
Figure 4E:
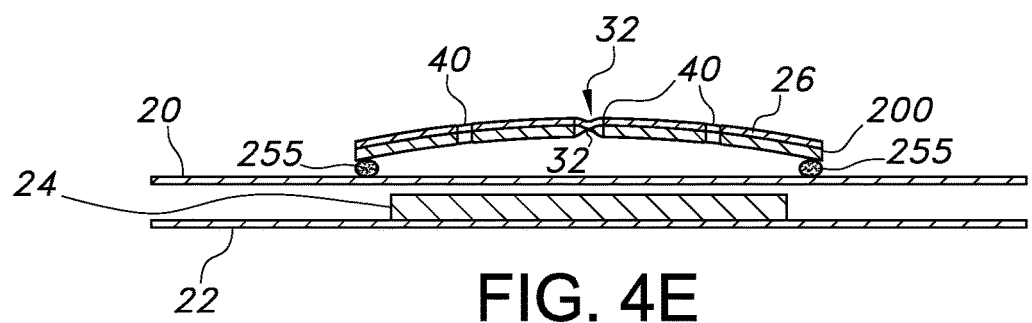
FIG. 4E illustrates an exploded, cross-sectional view of a further embodiment of the sanitary pad of the invention.

The liquid permeable first topsheet layer 26 desirably includes a fold or bend line 32, which may be present on either the garment-facing surface 26B (as seen in FIGS. 1 and 4A), the user-facing surface 26A (as seen in FIG. 4B) or both surfaces of the liquid permeable first topsheet layer 26 (FIG. 4E). Such fold or bend line 32 may be formed by several methods, including for example, traditional embossment techniques and spaced-apart, elongated slits. Such fold or bend line 32 may be continuous or discontinuous, and is desirably positioned along the article central longitudinal direction Lc. Desirably, such fold or bend line 32 has a transverse direction width of between about 1 mm and 3 mm. The fold or bend line 32 may be configured in a straight line as shown. The fold or bend line 32 may also be comprised of a series of spaced apart, relatively small embossment shapes or points, such as circular dots, that are aligned generally in a straight line along the central longitudinal direction. In one embodiment, the transverse direction width of such shapes or points is between about 1 mm and 3 mm, and such are each spaced apart along the longitudinal direction by a distance of between about 1 mm and 5 mm.

The liquid permeable first topsheet layer 26, defines at least one aperture opening 40 (FIG. 1), 60 (FIG. 2G) extending through the first topsheet layer entire thickness (in the Z direction). It should be reiterated that the liquid permeable first topsheet layer 26 is liquid permeable regardless of the presence of the at least one aperture opening 40, 60. Such at least one aperture opening 40, 60 is a continuous uninterrupted aperture opening which extends from the user-facing surface 26A of the liquid permeable first topsheet layer 26, through the first topsheet layer entire thickness, to the garment-facing surface 26B, and also to the user-facing surface 23A of the liquid permeable second topsheet layer 20, such that there is direct liquid communication from the user-facing surface 26A to the liquid permeable second topsheet layer 20 user-facing surface 23A. There is desirably a clear visual line of sight through the first topsheet layer aperture opening to the second topsheet layer user-facing surface. In one embodiment, at least the aperture opening(s) and optionally the second topsheet layer user-facing surface (through the opening(s)) are visible to an individual article user from at least the range of about 0.25 feet (0.075 meters) to about 3 feet (0.91 meters), when viewing the user-facing, topsheet surfaces of the absorbent article. In an alternative embodiment, such aperture openings 40, 60 are normally visible to an article user from a distance of at least 3 meters without aperture opening background color contrast (that is contrast between the aperture opening and the immediately surrounding article surfaces), or 5 meters, with aperture opening background color contrast.

Such "uninterrupted" opening is uninterrupted by any intermediate blocking material (such as fibrous or film material that could distort, slow, or otherwise interfere with the direct travel path of liquid from the liquid permeable first topsheet layer 26 to the liquid permeable second topsheet layer 20 through the opening 40, 60, or the viewing of the second topsheet layer through the first topsheet layer. As noted, in a desirable embodiment, a user of the article should be able to directly view the liquid permeable second topsheet layer (user-facing surface 23A), through either the entire dimension of, or at least a portion of the aperture opening 40, 60 of the liquid permeable first topsheet layer 26. Any printed features on the second topsheet layer, that are immediately beneath the aperture opening 40, 60 in the article Z direction, are also desirably seen through the aperture opening.

The at least one aperture opening(s) 40, 60 may be of any shape and may be singular or multiple in number. Multiple apertures 40 as shown in FIG. 1, may be of multiple sizes, but are desirably symmetrically positioned along the central longitudinal direction (axis) Lc. It is desirable in one embodiment, for the apertures to all be of the same shape if present as multiple apertures. Such apertures are shown in FIG. 1 as multiple sized circles, with larger circles positioned along the bend line 32.

While the embodiment illustrated in FIG. 1 shows aperture openings 40 symmetrically aligned along the fold or bend line 32, such need not be the case. Such aperture openings may be irregularly positioned in the liquid permeable first topsheet layer 26. Such aperture openings 40 are desirably formed using traditional cutting, or other mechanical puncturing/punching methods. It is desirable in one embodiment, for such apertures to not include tapered side edges or for such aperture walls to not extend beyond the plane of the first topsheet layer in the depth direction.

It is desirable in one embodiment, for the liquid permeable first topsheet layer 26 to be hydrophobic, alternatively, more hydrophobic than the liquid permeable second topsheet layer 20. Such difference in hydrophobicity can be accomplished either by utilizing the inherent nature of the topsheet layer materials selected, or by selective topographical treatment or polymeric melt formation treatment, such as by use of selective surfactant treatments on the second topsheet layer or hydrophobic treatments on the first topsheet layer. Such treatments are well known in the art and will therefore not otherwise be described.

In a desirable embodiment, as seen in FIG. 1, the liquid permeable first topsheet layer 26 includes overall dimensions that are smaller in length and width than the underlying liquid permeable second topsheet layer 20 and which first topsheet opposing lateral side edges 28 are positioned inward (closer to the central longitudinal axis/direction $L_c$) from both the opposing lateral side edges of the liquid permeable second topsheet layer 20 and the opposing lateral side edges of the pad 11. See for example, the smaller dimensioned first topsheet layer of FIGS. 3C and 3D. In the illustrated embodiment of FIG. 1, the liquid permeable first topsheet layer 26 is positioned in the initial liquid deposition region of the pad (i.e. the central insult region adjacent the wings, and along the central longitudinal and transverse directions) and as a result, the user's skin can come into contact with both the liquid permeable first topsheet layer 26 and the liquid permeable second topsheet layer 20, the latter of which is directly exposed to the user's skin beyond the peripheral side edges of the liquid permeable first topsheet layer 26. The liquid permeable first topsheet layer 26 appears to be "floating" above the liquid permeable second topsheet layer 20 as a result of the space or gap that can be formed between them as they partially separate from one another during article use.

It is desirable in one embodiment, for the length $L_1$ of the sanitary pad 10 to be between about 180 and 420 mm, more desirably between about 230 mm and 280 mm, and the length $L_2$ of the liquid permeable first topsheet layer 26 to be between about 80 mm and 330 mm, desirably between about 100 mm and 120 mm. In one embodiment, it is desirable for the ratio $L_2$ to $L_1$ to be between about 0.2 to 1.0, desirably between about 0.4 to 0.8. The transverse direction width T2 of the first topsheet layer is desirably shorter than that T1 of the absorbent article, but may be of the same width.

As can be seen in the various illustrated embodiments, the aperture openings 40 can be present as a series of proximately located holes 40 (FIG. 1) or singular holes 60. Such holes are still macro-openings that are desirably positioned along the central longitudinal direction of the pad and adjacent the wings if wings 14 are present, so as to be located in a pad central fluid insult region. Desirably in one embodiment, such proximately located series of holes are positioned over a subjacent apertured layer, itself with at least one macro-opening aligned with the aperture opening (s) of the first topsheet layer. Such a subjacent layer can further assist fluid in traveling quickly to the storage component of a pad after being exuded by a user. Such a subjacent apertured layer with higher profile along the Z direction, is illustrated as 80 in FIG. 4D, and can form a raised area in the center of a pad.

If the aperture openings 40 are present as a series of proximately located openings (as in FIG. 1), desirably in one embodiment the multiple holes 40 extend cumulatively a distance L3 of between about 30 mm and 300 mm along the first topsheet layer length, alternatively between about 40 mm and 100 mm. Such holes desirably in one embodiment, extend cumulatively along a transverse distance T3 of about 20 mm and 60 mm, alternatively between about 20 mm and 40 mm. In such an embodiment, the individual holes (of the multiple hole embodiment) are desirably spaced apart from one another by between about 3 mm and 20 mm, alternatively, between about 3 and 10 mm. If such aperture openings 40 are present as a series of proximately located holes, such holes can be present in a variety of shapes and sizes or in the same shapes and/or sizes. For example, in FIG. 1, similarly sized and shaped aperture openings 40 are circular. Differently sized, but similarly shaped aperture openings 40 are shown in FIG. 2A. Differently shaped and sized aperture openings 40 are shown in FIG. 2B, in which relatively larger, oblong/oval-shaped openings are positioned on the bend line 32 and relatively smaller, circular-shaped openings are present off of the bend line 32. Square and rectangular-shaped openings are illustrated in FIG. 2C. For relatively smaller sized openings (such as illustrated circular openings), it is desirable in one embodiment for such proximately located circular openings to have a diameter of between about 2 mm and 10 mm, alternatively, between about 2 mm and 5 mm. As seen in the figures, the proximate openings 40 may be positioned in an overall configuration, such as for example, an overall oval arrangement.

If such aperture opening 60 is present as a singular opening (as in FIG. 2G) defined by a first topsheet layer interior edge 26C, such opening may also be of a variety of sizes and shapes, but is desirably of a curvilinear shape such as oval, oblong, or circular, and is positioned along the central longitudinal direction, and adjacent the wings, if such wings are present. If present as a relatively large macro-aperture opening 60 (as in FIG. 2G), the transverse direction width T3 (FIG. 2G) of such opening is in one embodiment, between about 20 mm and 60 mm, alternatively, between about 20 mm and 40 mm. The longitudinal direction length L3 of such opening is in one embodiment, between about 30 mm and 100 mm, alternatively, between about 50 mm and 70 mm. Desirably, such singular opening is sized to encircle the perineal or vaginal region of a user, such as to limit the first topsheet layer contact on the regions of a user's body that are most likely to exude liquid/fluid. As with the previously described "proximate multiple hole" embodiments, and even more so, such exuded liquid will travel more quickly to the storage component of the absorbent article through said uninterrupted singular opening. As with the prior embodiments with relatively smaller uninterrupted holes, in another embodiment a lower layer within the article (along the depth direction) can include a raised profile and also define its own macro-opening 83 such that a funnel-like structure is created between the first topsheet layer opening 40 and the lower apertured layer 80. Such funnel-like structure will enhance delivery of exudate directly to the storage component of the absorbent article. Whether such opening is of singular or multiple formats, such opening extends through the entire thickness of the liquid permeable first topsheet layer and allows the viewing of the second topsheet layer through the first topsheet layer. If the embodiment includes the raised Z-direction profile lower layer 80, such lower layer can provide a hump-like feature along the central longitudinal direction of the article to enhance contact of the second topsheet layer with the skin of the user selectively, either selectively within or adjacent to the liquid permeable first topsheet layer opening(s) 40, 60.

Desirably in one embodiment, the transverse direction width $T_1$ of the pad 10, between pad opposing lateral side edges 11 is between about 70 mm and 100 mm, alternatively between about 80 and 90 mm. Desirably, the transverse direction width $T_2$ of the liquid permeable first topsheet layer 26, between the first topsheet layer opposing lateral side edges 28 is between about 45 mm and 75 mm, alternatively between about 55 mm and 65 mm. Desirably in one embodiment, the transverse direction width $T_4$ of either the absorbent core layer structure 24 or other fluid handling layers is between about 10 mm and 100 mm, alternatively between about 40 mm and 80 mm. In some embodiments, it may be more desirable for the lateral side edges of the absorbent core layer structure or other fluid handling layers to lie laterally beyond the opposing lateral side edges 28 of the liquid permeable first topsheet layer 26 (farther from the central longitudinal axis), when viewed along the pad Z direction, while in other embodiments, it may be desirable for the lateral side edges of either the absorbent core layer structure 24 or other fluid handling layers 80 to lie inside the opposing lateral side edges 28 of the liquid permeable first topsheet layer 26. At least one garment fastening patch 260, such as an adhesive or hook-and-loop type patch, may be present on one or more of the underside surfaces of the liquid impermeable backsheet layer 22, such as in the wing areas or along the longitudinal center direction of the article, to allow for fastening of the article to a user's undergarments. Such fastening patch 260 may be covered with a release sheet (not shown) for preservation of adhesive while not in use. Also, a peripheral seal region 261 is desirably present along the peripheral edges of the liquid permeable second topsheet layer 20 and liquid impermeable backsheet layer 22, such that the absorbent layer 24 perimeter is sandwiched and sealed between such layers, thereby reducing side leakage at the article peripheral side edges. Such peripheral seal 261 may be accomplished by any number of traditional bonding techniques such as for example, adhesive, thermal, or ultrasonic bonding techniques.

An exploded cross-sectional view of the embodiment of FIG. 1 along line 4A-4A is illustrated in FIG. 4A. As can be seen in the figure, some of the aperture openings 40 are aligned on the bend line 32 along the central longitudinal axis of the article. The bend line 32 is an embossed flexure line along the garment-facing side 26B of the liquid permeable first topsheet layer. While lines of adhesive 255 are shown as fastening the folded edge portions 27 of the first topsheet layer 26 to the user-facing surface of the second topsheet layer 20, any other bonding technique can be used, such as for example, thermal and ultrasonic bonds.

For ease of reference, FIG. 2A illustrates a top plan view of the user-facing surface of only the liquid permeable first topsheet layer 26, of the sanitary pad of FIG. 1. As seen in the figure, multiple sized circular aperture openings 40 are situated in a generally overall oval and symmetrical arrangement about the bend line 32. The circular aperture openings are situated in three distinct rows, with two rows of relatively smaller circular aperture openings positioned off of the bend line, and one row of relatively larger circular aperture openings positioned directly on the bend line 32.

In FIG. 2B, a top plan view of the user-facing surface of an alternative embodiment of only the liquid permeable first topsheet layer 26 is illustrated. As with FIG. 2A, such liquid permeable first topsheet layer 26 is shown separated from the underlying pad layers. As can be seen in FIG. 2B, the uninterrupted aperture openings 40 include two differently shaped and sized aperture openings 41 and 42. One aperture opening shape is of a relatively larger oblong or elliptical configuration 41, while the other is of a relatively smaller circular configuration 42. As with the prior figure, only some of the aperture openings (the elliptically shaped aperture openings 41) are aligned on the fold line 32, while all are symmetrically placed about the central longitudinal direction/axis. In this alternative embodiment, the longitudinally directed ends 29 include a simplified curved edge as compared to the end edge of FIGS. 1 and 2A which included a scalloped design of multiple curved sections. As with FIG. 2A, the folded-under longitudinal side edges 27 are shorter in length 27A than the length of the opposing lateral side edges 28 and are positioned generally centered along the opposing lateral side edges 28.

In yet another alternative embodiment, as seen in FIG. 2C, a top plan view of the user-facing surface of only a liquid permeable first topsheet layer 26 (separated from the pad) is illustrated in an overall rectangular configuration. A single row of differently shaped and sized aperture openings (in square and rectangular configurations) is present on the fold line 32. The longitudinally directed end edges 29 are of uniform length across the transverse direction T of the liquid permeable first topsheet layer 26. The folded-under edges 27 have a folded-under length 27A that is the same size as the opposing lateral side edges 28 of the liquid permeable first topsheet layer 26. The mechanism (such as adhesive) that is used to bond such folded-under edges to the second topsheet layer, may extend along the full length of the edge or a partial length of the folded under edge.

Figure 2D:
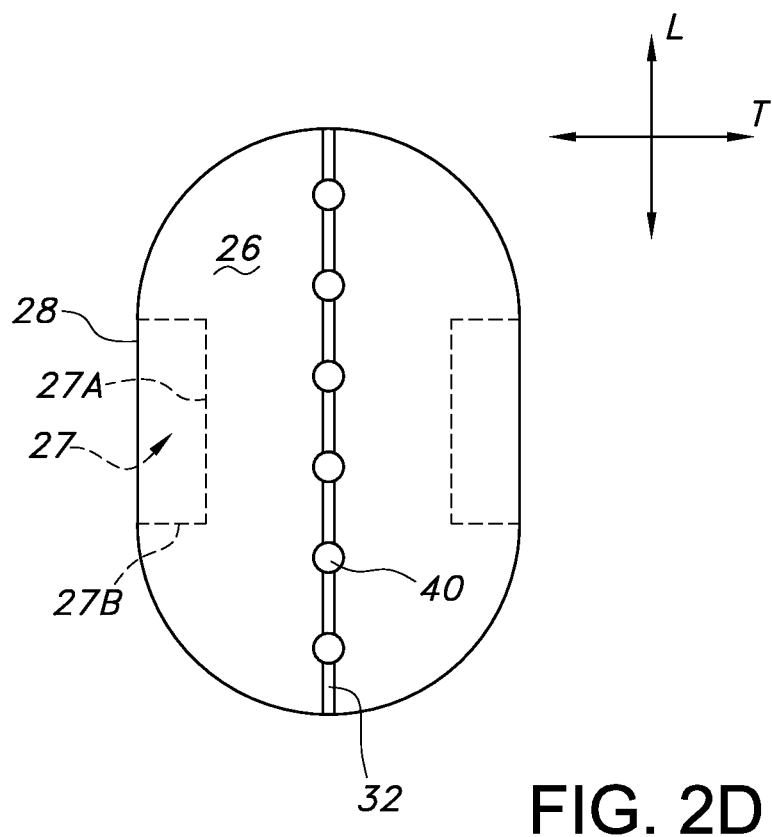
FIG. 2D illustrates a top plan view of the user-facing surface of still another alternative embodiment of only the partially separable liquid permeable first topsheet layer of the sanitary pad of FIG. 1.

In still another alternative embodiment as seen in FIG. 2D, a top plan view of only the user-facing surface of a liquid permeable first topsheet layer 26 is also shown separated from an underlying pad structure for ease of viewing. In this alternative embodiment, similarly shaped and sized circular aperture openings 40 are aligned along a fold line 32 on the liquid permeable first topsheet layer 26. Relatively smaller folded-under edges 27 are present along the opposing lateral side edges 28 of the liquid permeable first topsheet layer 26. The folded-under edges 27 are significantly shorter 27A with respect to the overall opposing lateral side edge 28 length of the first topsheet layer 26 than previously illustrated embodiments, but are of similar relative widths 27B. If present in the embodiment, these folded-under edges 27 may include one or more folds visible from the article Z direction. For example, as seen in FIGS. 4C and 4D there are two folds, one present along each opposing lateral side edge 28. In alternative embodiments, multiple Z-type fold configurations are also contemplated for each opposing lateral side edge along the article Z-direction. It should be appreciated that the views of FIGS. 2A-2D illustrate the user-facing surface of the first topsheet layer 26 only.

Figure 2E:
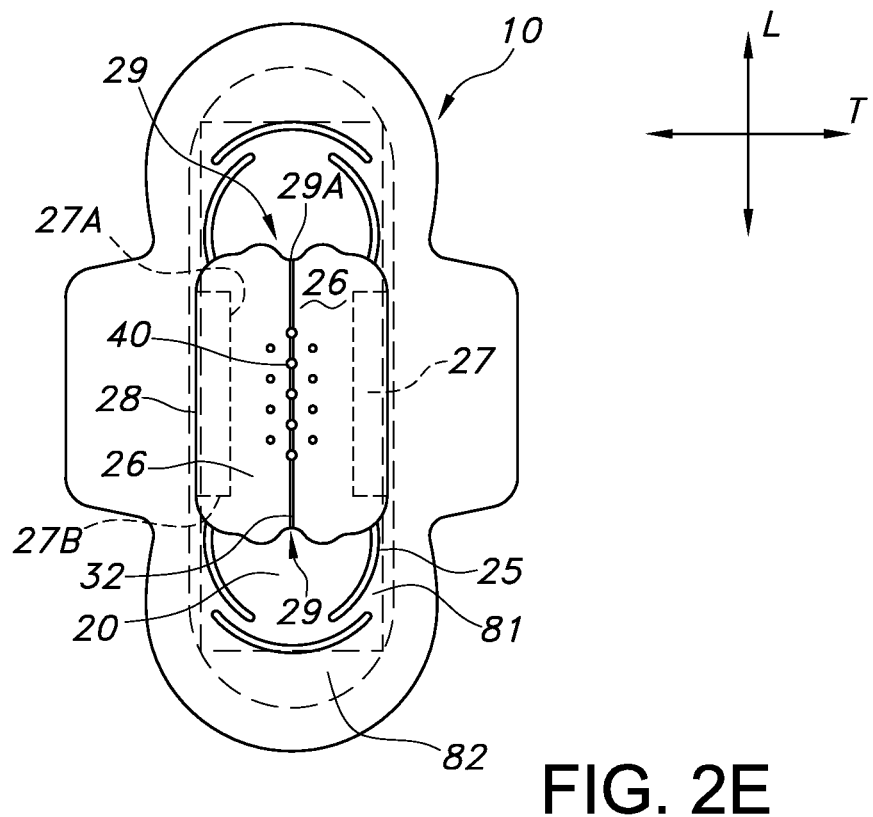
FIG. 2E illustrates a top plan view of the user-facing surface of another alternative embodiment of the sanitary pad of FIG. 1.
Figure 2F:
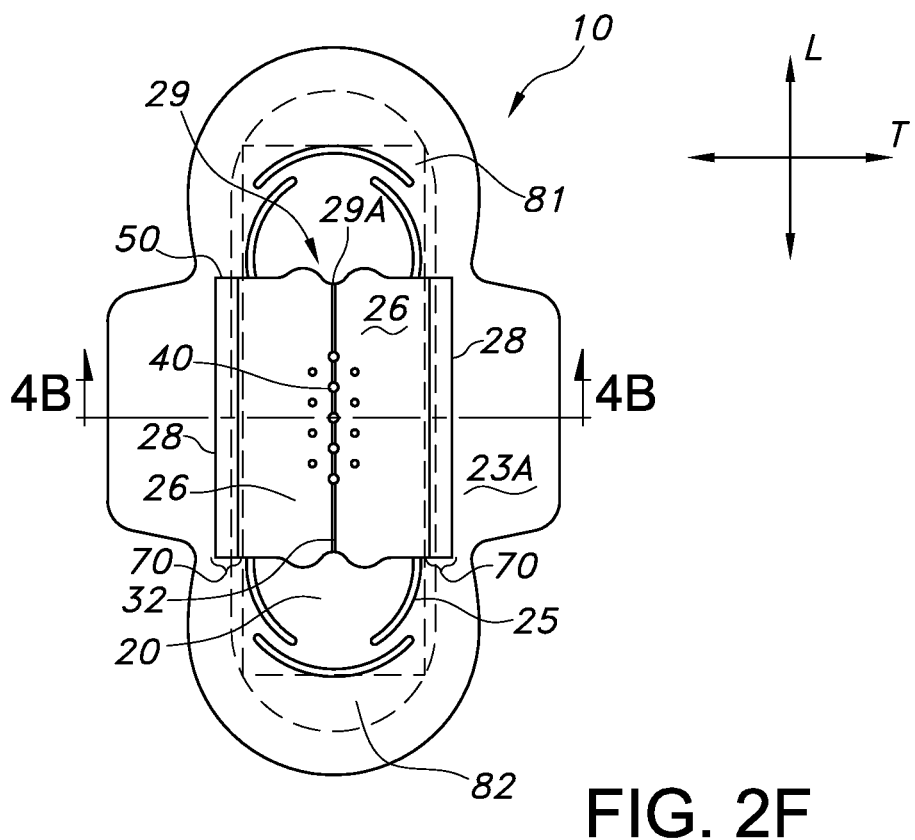
FIG. 2F illustrates a top plan view of the user-facing surface of a further alternative embodiment of the sanitary pad of FIG. 1.

In yet another alternative embodiment, a top plan view of the user-facing surface of an entire sanitary pad 10 in accordance with the invention is shown in FIG. 2E. As seen in the figure, the opposing longitudinally directed ends 29 of the liquid permeable first topsheet layer 26 include an end recess 29A with which the fold or bend line 32 is aligned. Circularly shaped aperture openings 40 are present both on and off the fold line 32. The ends 29 also include multiple curved sections. The folded-under edges 27 are shorter than the opposing lateral side edges 28 of the liquid permeable first topsheet layer 26 in this illustrated embodiment.

In still another alternative embodiment of the sanitary pad of FIG. 1 as seen in FIG. 2F, such a liquid permeable first topsheet layer 26 includes opposing lateral side edges 28 that are bonded along their length to an underlying liquid permeable second topsheet layer 20 without the use of folded-under edges. In particular, opposing attachment zones 70 are adhesive bonded areas along the garment-facing side surface of the opposing lateral side edges of the liquid permeable first topsheet layer 26.

Such bonded areas may be at the side edges themselves or adjacent to the opposing lateral side edges 28, and are bonded to the liquid permeable second topsheet layer 20 user-facing surface 23A without use of Z-folds. Such bonding may be accomplished via any traditional bonding technique such as thermal, adhesive or ultrasonic bonding, although as can be seen in the exploded cross-sectional view at line 4B-4B of this embodiment in FIG. 4B, a line of adhesive 255 is used. The opposing lateral side edges 28 of the liquid permeable first topsheet layer 26 are illustrated as being straight edges in this embodiment. The opposing longitudinal ends 29 of the liquid permeable first topsheet layer 26 also include primarily straight edges 50 with a centrally located end recess 29A along the transverse direction, which recess is aligned with the bend line 32.

Figure 2G:
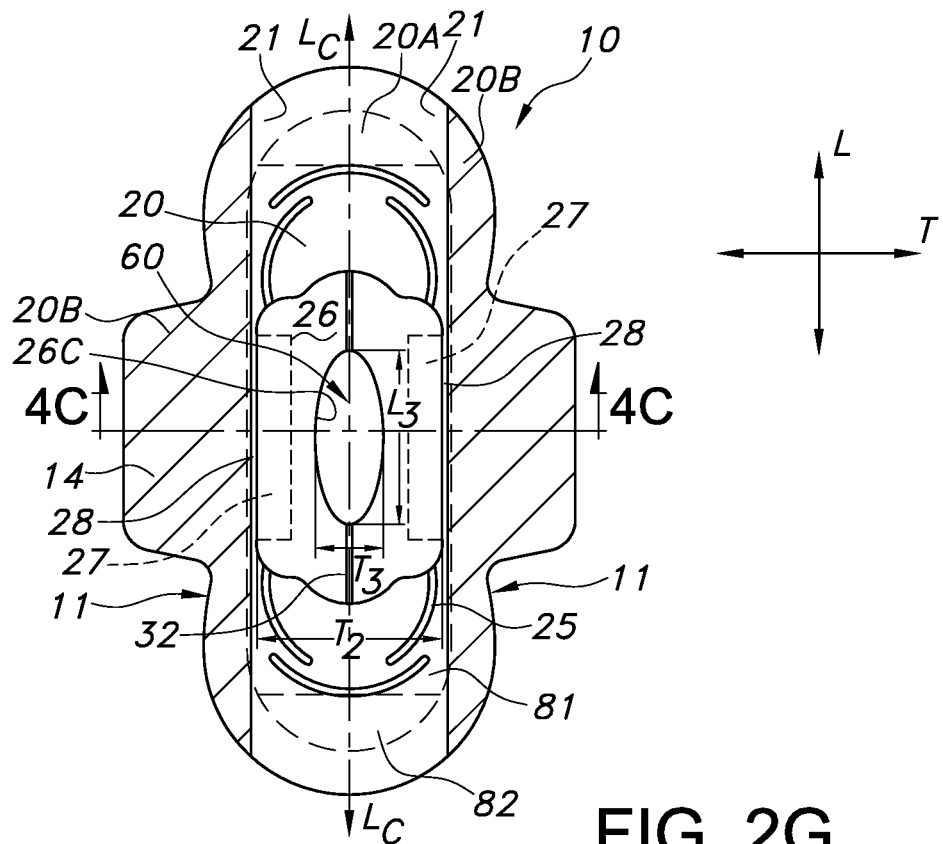
FIG. 2G illustrates a top plan view of the user-facing surface of a further alternative embodiment of the sanitary pad of FIG. 1.

A top plan view of yet another alternative embodiment of a sanitary pad in accordance with the invention is illustrated in FIG. 2G. In this figure, as with previous figures, the user facing surface of the entire sanitary pad 10 is illustrated. Unlike previous embodiments, the sanitary pad 10 in this figure includes a liquid permeable second topsheet layer 20, which itself includes two layers 20A and 20B positioned along the article transverse direction. A central longitudinally directed topsheet layer 20A is situated as straddling the central longitudinal axis/direction of the sanitary pad 10. Two side topsheet layers 20B (or side covers) are situated along each lateral side edge 11 of the pad. The two side topsheet layers 20B are shown shaded for ease of reference, but may also be differently colored than the central section. The side topsheet layers 20B are bonded over the side edges of the central longitudinally directed topsheet layer 20A, using any traditional bonding technique. The liquid permeable first topsheet layer 26 is shown with folded-under edges 27 that are bonded to the central longitudinally directed topsheet layer 20A in the central region of the pad. The liquid permeable first topsheet layer 26 defines a single, centrally located oval aperture opening 60 defined by an interior edge 26C of the first topsheet layer 26, which aperture opening allows direct and uninterrupted liquid communication from the liquid permeable first topsheet layer 26 user-facing surface, to the underlying user-facing surface of the liquid permeable second topsheet layer 20A. As with the multiple, proximate aperture openings 40 of earlier embodiments, such singular aperture opening 60 extends through the entire first topsheet layer thickness (in the Z direction). The defined oval aperture opening 60 is symmetrically positioned within the liquid permeable first topsheet layer 26 about the central longitudinal axis of the pad.

Figure 3C:
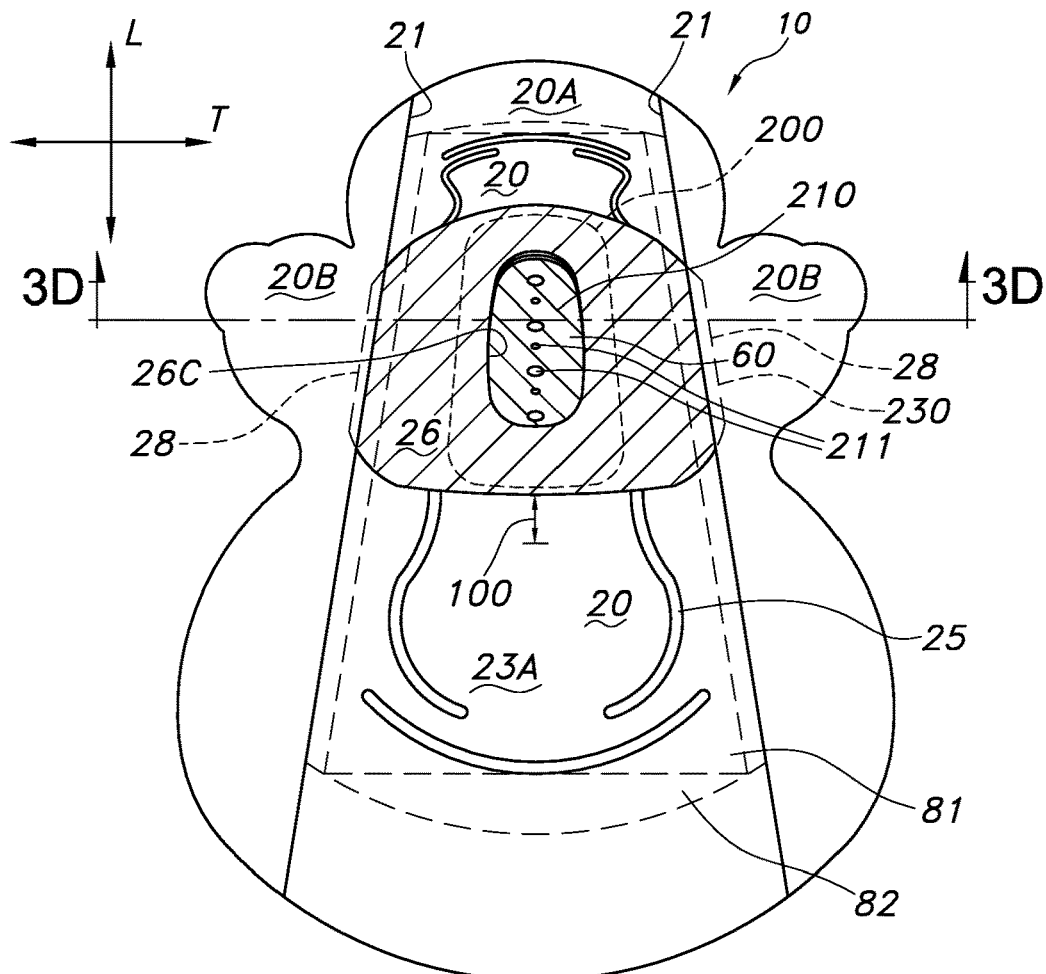
FIG. 3C illustrates a top surface perspective view of another alternative embodiment of a sanitary pad in accordance with the invention in which an asymmetrical pad is shown.
Figure 3D:
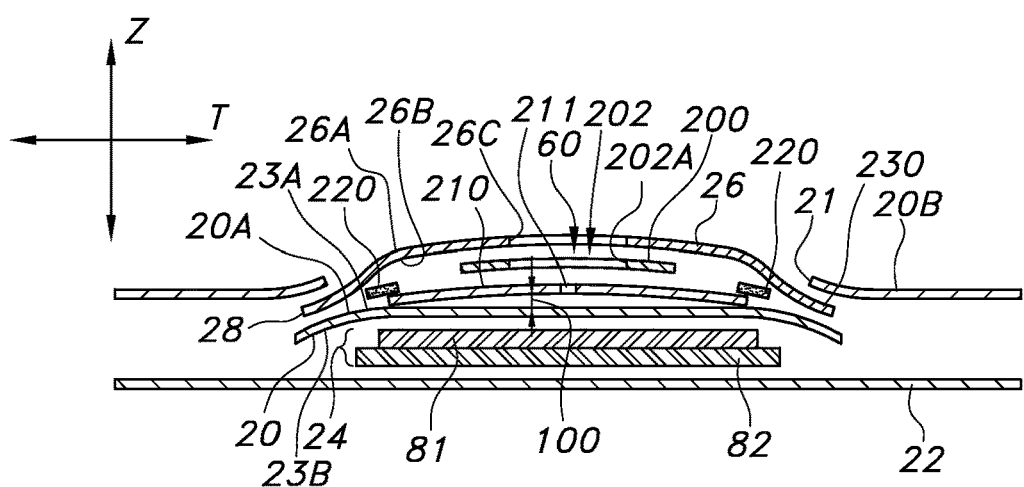
FIG. 3D illustrates an exploded, cross-sectional view of the alternative embodiment of the sanitary pad of FIG. 3C, taken along line 3D-3D.

The transverse width $T_2$ of the liquid permeable first topsheet layer 26 between the opposing lateral side edges 28, is in one embodiment, narrower than, or approximately equal (as shown) to the transverse direction distance between the side topsheet layers 20B (side cover layers) inside edges 21. In an alternative, such transverse width $T_2$ is wider than the distance between inside edges 21, such that there is overlap of the various edges 27, 28 of the liquid permeable first topsheet layer 26 with the side topsheet layer inside edges 21. Alternatively, such folded under edges 27 and opposing lateral side edges 28 extend across the inside edges 21. A two layer absorbent core structure 81, 82 is shown in phantom. In still a further alternative embodiment, such overlapping inside edges 21 may be positioned over and above the opposing lateral side edges 28 (in the Z direction) of a liquid permeable first topsheet layer 26, without the presence of folded-under edges 27 on a liquid permeable first topsheet layer 26. Such concept is generally illustrated in FIGS. 3C and 3D as will be later described.

An exploded cross-sectional view of FIG. 2G at line 4C-4C is illustrated in FIG. 4C. As can be seen in this figure, the central longitudinal topsheet layer 20A is bonded to side topsheet layers 20B at regions 250. The folded under edges 27 are positioned inward of side topsheet layer inside edges 21 and are bonded to the second topsheet layer by a line of adhesive 255.

Figure 2H:
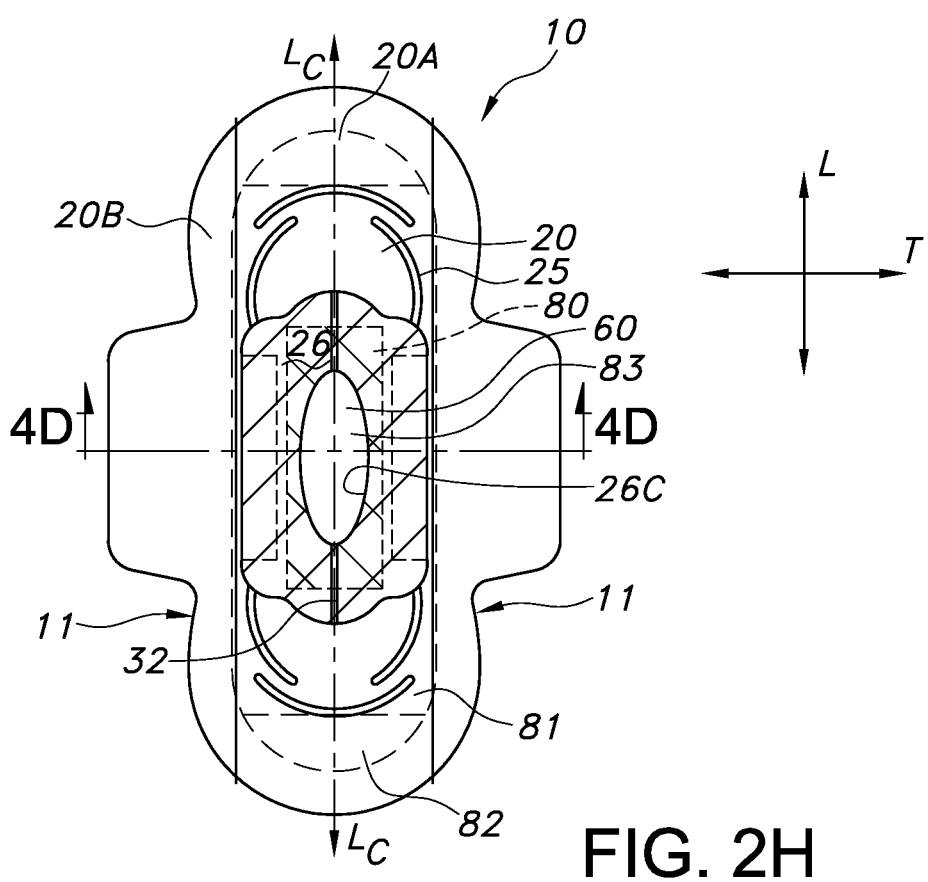
FIG. 2H illustrates a top plan view of the user-facing surface of still another alternative embodiment of the sanitary pad of FIG. 1.

A top plan view of yet another alternative embodiment of a sanitary pad 10 in accordance with the invention is illustrated in FIG. 2H. In this figure, as with previous figures, the entire user-facing surface of the sanitary pad 10 is illustrated. As with the immediately previous embodiment, the sanitary pad 10 in this figure includes a liquid permeable second topsheet layer 20, which itself includes two layers 20A and 20B. A central, longitudinally directed topsheet layer 20A is situated about the central longitudinal direction/axis of the sanitary pad 10. Two side topsheet layers 20B are situated along each lateral side edge 11 of the pad 10. The side topsheet layers 20B are bonded over the side edges of the central longitudinally directed topsheet layer 20A, using any traditional bonding technique. The liquid permeable first topsheet layer 26 is shown with folded-under edges 27 that are bonded to the central longitudinally directed topsheet layer 20A. The liquid permeable first topsheet layer 26 includes a single, centrally-located oval aperture opening 60 which allows liquid communication from the liquid permeable first topsheet layer user-facing surface, directly to the underlying user-facing surface of the liquid permeable second topsheet layer 20A. The oval opening 60 is symmetrically positioned within the liquid permeable first topsheet layer 26 about the central longitudinal axis of the pad and allows for the uninterrupted communication of liquid from the user to the second topsheet layer (and also the viewing from the user-facing surface of the pad of the second topsheet layer 20A through the opening). The liquid permeable first topsheet layer 26 is colored or otherwise visually distinguished (such as textured) from the underlying liquid permeable second topsheet layers 20A, 20B so as to emphasize the layer's presence on the pad and also to assist the user in placement of the first topsheet layer under that portion of the user's perineal region where liquid exudes. The color contrasting background of the second topsheet layer 20A beneath the opening 60, allows for recognition of the aperture opening feature from a distance of as great as 5 meters. As seen in the exploded cross-sectional view of this embodiment in FIG. 4D along lines 4D-4D, an underlying fluid handling layer 80 above the absorbent core layers 24, defines another uninterrupted aperture opening 83 which is aligned with the liquid permeable first topsheet layer 26 oval opening 60 in the Z direction. Such aligned opening is in one embodiment, of the same shape and size as the opening 60 defined by the liquid permeable first topsheet layer 26, but need not be. Such aligned opening will allow for the more rapid movement of liquid through the sanitary pad 10 to the absorbent core layer structure 24 beneath, and creates a funnel-like structure along the Z direction of the pad. In this illustrated embodiment, the absorbent core layer structure 24 includes two separate layers 81, 82 each having different lateral dimensions, one 81 being narrower than the transverse width $T_2$ of the liquid permeable first topsheet layer 26, and the other 82 being wider or equal to the transverse width $T_2$ of the liquid permeable first topsheet layer 26. As also seen in the cross-sectional view, the liquid permeable first topsheet layer 26, is actually comprised of two separate topsheet layers 90, 91 each having an aligned aperture opening of similar oval shape and size, so as to allow for the uninterrupted flow of liquid from a user to the second topsheet layer 20. It is desirable in such embodiment, that both topsheet layers (including the second topsheet layer) be hydrophobic. The interiorly situated, apertured lower layer 80 with aligned oval opening 83 in the embodiment of FIG. 4D, may include a relatively larger height than other layers within the article, such as to create a hump-like feature in the central region of the pad. Such a hump-like feature may assist in maintaining contact of only that region of the pad adjacent a user's body in the perineal or vaginal region.

A top surface perspective view of still another alternative embodiment of the sanitary pad 10 is illustrated in FIG. 3A. As can be seen in the Figure, the liquid permeable first topsheet layer 26 is elevated by the bend line along the article central longitudinal axis/direction by a distance 100 above the liquid permeable second topsheet layer 20. The highest elevation of the liquid permeable first topsheet layer 26 above the second topsheet layer 20 corresponds to the location of the bend line 32. Such elevation is desirably in one embodiment, between about 3 mm and 15 mm, alternatively, between about 5 and 10 mm above the user-facing surface of the liquid permeable second topsheet layer 20. Such elevation creates a spatial gap or void between the two layers, which gap can enhance air circulation through the article and reduce rewet sensation during prolonged article use. Such gap also provides emotional comfort to the user with the recognition that a potential separation will occur between the topsheet and the storage component. The elevation is enhanced by a combination of the bend line feature, z-folded edges (if present), the selection of topsheet layer (and directly attached layer) materials, and the lateral compression of the article during use.

Desirably in one embodiment, the transverse width of the bend line 32 is between about 1 mm and 7 mm, alternatively, between about 2 mm and 7 mm, alternatively between about 2 mm and 5 mm. As can also be seen in this embodiment, the liquid permeable first topsheet layer 26 is bonded via a folded under portion 27 to a central longitudinal topsheet layer 20A, and includes opposing lateral side edges 28 which are positioned inwardly from inside edges 21. Multiple, relatively smaller oval aperture openings 40 are situated on and about the bend line 32.

A side perspective view of still another alternative embodiment of a sanitary pad is illustrated in FIG. 3B. As can be seen in the figure, a centrally positioned single oval aperture opening 60 is positioned in the liquid permeable first topsheet layer 26. The layer relies on folded under portions 27 and the bend line 32 to help it elevate a desired distance 100 above the liquid permeable second topsheet layer 20 (and specifically a central longitudinal topsheet layer 20A).

In an alternative, such folded under portions 27 can be eliminated, and the liquid permeable first topsheet layer 26 may be elevated above the liquid permeable second topsheet layer 20 along the central longitudinal direction/axis, by use of a combination of particular topsheet material (along the article transverse direction) and closer opposing attachment zones such as by adhesive lines 255 adjacent the underside of first topsheet layer 26 lateral side edges (as seen in FIG. 4E).

Rather than including a two layered topsheet in the structure (as in FIG. 4D, in which such two topsheet layers do not serve as storage components), in an alternative embodiment, a second attached layer 200 may be a liquid transfer layer 200. Again, as with the single and two layer topsheet embodiments, such transfer layer embodiment still does not serve as a storage component. Rather such layer serves to help direct fluid/liquid ultimately to the storage component 24. However, such transfer layer may also provide enhanced rigidity to the first topsheet layer structure in order to help it maintain a predisposition to an elevated configuration.

In yet still a further alternative embodiment of a sanitary pad 10, a top surface perspective view of an asymmetrical pad is illustrated in FIG. 3C. In this alternative embodiment, the liquid permeable first topsheet layer 26 is visually distinguishable from the liquid permeable second topsheet layer 20. The second topsheet layer 20 includes a central longitudinal topsheet layer 20A and two side topsheet layers 20B. Further, the opposing lateral side edges 28 of the liquid permeable first topsheet layer 28 extend under the side topsheet layers 20B in the Z direction, at side regions 230. While not included in this figure, embossment patterns may be positioned over these side regions 230 to help secure the layers together. Adhesive lines 220 (as seen in FIG. 3D) may optionally also be used to bond the layers together. Alternatively, such opposing lateral side edges 28 need not extend under the side topsheet layers 20B.

A seen in this figure, a fluid transfer or directing layer 200 may optionally be present in the article, subjacent to the liquid permeable first topsheet layer 26 in the article Z direction. The transfer layer 200 desirably includes a singular, aligned aperture opening 202 defined by transfer layer interior edge 202A. Such aperture opening 202 is sized, shaped, and positioned in alignment with the liquid permeable first topsheet layer singular aperture opening 60 (in this case an oval opening). Such fluid transfer layer 200 may itself be comprised of multiple layers (which are not storage components) and may be printed or otherwise colored so as to further distinguish it from the liquid permeable first topsheet layer 26, and to also emphasize the presence of the uninterrupted singular aperture opening 60 feature. As illustrated in the figure, the fluid transfer layer 200 may be smaller in overall dimension than the overlaying liquid permeable first topsheet layer 26 to which it is directly attached, desirably fully along the transfer layer length and width dimensions. Such attachment may be by any known bonding method, such as for example adhesive, thermal, and ultrasonic bonding. By including a relatively smaller dimensioned fluid transfer layer 200 of shorter length, narrower width, or a combination, than the liquid permeable first topsheet layer 26, additional rigidity can be provided to the overall "floating" first topsheet layer structure. As an example, the fluid transfer layer may be made from a lofty hydrophobic TABCW material having a basis weight of between about 20 gsm and 50 gsm. Alternatively, such fluid transfer layer may be made from a hydrophobic airlaid layer having a basis weight of between about 50 gsm and 120 gsm.

Optionally, an additional liquid permeable topsheet layer 210 is positioned and attached either immediately subjacent the fluid transfer layer 200 in the article Z direction (as seen in the exploded cross-sectional view along line 3D-3D of FIG. 3D) or immediately subjacent the liquid permeable first topsheet layer 26 itself (not shown). The additional liquid permeable topsheet layer 210 is desirably bonded so as to cover the underside, garment-facing surfaces of both the narrower fluid transfer layer 200 and the liquid permeable first topsheet layer 26 (garment-facing surface 26B). Such fluid transfer layer 200 is therefore desirably sandwiched between the liquid permeable first topsheet layer 26 and the additional liquid permeable topsheet layer 210. Such bonded laminate is itself partially separable (as a unit) from the underlying liquid permeable second topsheet layer 20, such as by height 100. It is desirable in one embodiment, for the additional liquid permeable topsheet layer to also be less hydrophilic than the liquid permeable second topsheet layer 20, and in fact, for it to be hydrophobic.

As with previously described embodiments, a continuous or partial spatial gap is present between opposing laterally positioned attachment zones (bonded regions) holding the first topsheet layer 26 (and attached layers as a unit) to the second topsheet layer 20, such that a separation space of a distance 100 may be formed between the liquid permeable first topsheet layer 26 and the liquid permeable second topsheet 20 layer during article use. This space forms as the first topsheet layer 26 lifts away from the second topsheet layer 20 between the opposing lateral side edges 28, such as a result of layer predisposition, upon compression of the article opposing lateral side edges during use or a combination of both. The additional liquid permeable topsheet layer 210 is situated between the liquid permeable first topsheet layer 26 and the liquid permeable second topsheet layer 20. The additional liquid permeable topsheet layer 210 includes at least one aperture opening 211 that is aligned with the singular aperture opening 60 of the liquid permeable first topsheet layer 26 (and also the transfer layer opening 202 if present) such that an uninterrupted opening extends directly to the user-facing surface 23A of the liquid permeable second topsheet layer 20, without visual blockage or liquid flow interference from any intermediate layer at least in some portions of the larger singular opening 60. The additional liquid permeable topsheet layer 210, may include a single aligned aperture opening or multiple aligned aperture openings as shown in FIG. 3C. Such multiple aperture openings may be of similar size and shape or of different sizes and shapes. In the illustrated embodiment of FIG. 3C, differently sized circular aperture openings 211 are shown in the additional liquid permeable topsheet layer 210. It is desirable in one embodiment, for the additional liquid permeable topsheet layer to be transparent so as to allow the user to further view the underlying liquid permeable second topsheet layer 20, user-facing surface 23A (and alternatively, layers subjacent to it) clearly from the user-facing surface 26A of the liquid permeable first topsheet layer 26 (through the aperture opening 60). Desirably in one embodiment, the additional liquid permeable topsheet layer 210 is a dual-apertured film, in which one set of micro-apertures of a first size (not shown) is formed by a first process, such as by vacuum formation, and a second larger set of apertures 211 is formed by a second process, such as for example by a cutting or punching process. Such additional liquid permeable topsheet layer 210 may also in an alternative embodiment, be an apertured nonwoven web. As with other layers (200) that are attached along their full length, to the first topsheet layer 26, such additional liquid permeable topsheet layer 210 is desirably hydrophobic.

It should also be recognized that each of the previously described absorbent article components may be printed or colored (such as desirably on the garment-facing side surfaces) for the purposes of highlighting the presence of the various layer aperture opening features, or for general aesthetic reasons. For instance, intermediate layers between the liquid permeable first topsheet layer 26 and the liquid permeable second topsheet layer 20 may be highlighted with a color in order to accentuate the uninterrupted opening(s) between the two topsheet layers. Similarly, fluid handling layers 80, and in particular, layers with aperture openings that are aligned with the aperture openings of the liquid permeable first topsheet layer 26 can also be highlighted in some embodiments to accentuate such opening features and to assist in the article placement under a user's perineal or vaginal area.

While not shown in the exploded cross-sectional views except for at a few discrete locations, conventional construction adhesive may hold the various layers together, particularly at their opposing lateral side edges, in addition to other bonding techniques, such as thermal bonding, ultrasonic bonding, mechanical bonding, hydroentangling or a combination thereof. Such construction adhesive should not be placed so as to block the direct passage of liquid through the aperture openings, or to prevent the separation and rising of the liquid permeable first topsheet layer 26 above the liquid permeable second topsheet layer 20 as heretofore described.

The liquid permeable first topsheet layer 26 may be manufactured from any number of conventional materials commonly used as a user-facing surface on an absorbent article. For example, non-limiting examples of such hydrophobic first topsheet materials include fibrous nonwoven sheet materials, such as spunbond, spunlace, meltblown, and carded web materials (such as thermally bonded carded webs (TBCW), through-air bonded carded webs (TABCW)), fibrous woven sheet materials, micro-apertured polyolefinic film or apertured fibrous nonwoven materials (single and dual apertured), and laminate combinations of the foregoing materials. Further, monolayered or multilayered sheet materials of the foregoing can also be used as the liquid permeable first topsheet layer. Particularly, carded web materials may be made from staple, bicomponent fibers as are known in the art. Further, such liquid permeable first topsheet layer 26 may include directly attached thereto, a variety of layers (such as a topsheet layer and transfer layer laminate) that partially separate and rise above the liquid permeable second topsheet layer 20 as a unit, but which layers do not encompass storage components. Materials that may be used in the first topsheet layer 26 include synthetic fibers, such as polyolefinic materials. Such first topsheet layers may be embossed as previously noted. In one embodiment, the liquid permeable first topsheet layer 26 desirably includes a dual apertured film and nonwoven laminate.

Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety. Desirably, such topsheet layer materials are either inherently hydrophobic based on their composition, or made so with hydrophobic treatments. Alternatively, such first topsheet layer materials are more hydrophobic than the second topsheet layer materials. Further examples of hydrophobic topsheet layer materials and other absorbent article internal layers may be found in U.S. Pat. No. 8,383,877 to Singh Kainth et al., and United States patent publication US2013/0197462 to Abuto et al. each of which are incorporated herein in their entirety by reference thereto, for purposes not inconsistent herewith.

The liquid permeable second topsheet layer 20 may be made from natural fibers or similar materials as previously described with respect to the first topsheet layer, desirably as long as they have been treated so as to impart some level of hydrophilicity, alternatively such that they are more hydrophilic (less hydrophobic) than said first topsheet layer 26. The liquid permeable second topsheet layer 20 may also be made from two or more different nonwoven or film materials at least one of which is inherently hydrophilic or which has been treated to provide such property, with the different materials placed in separate locations laterally across the second topsheet layer 20 and along the absorbent article transverse direction. For example, the topsheet layer 20 may be a two layer (such as in the same or two different horizontal planes) or multi-component material with a central longitudinally directed section as described in the figures positioned along and straddling the central longitudinal axis of the article, with lateral side-topsheet sections 20B flanking and joined to each side (or side longitudinal edge) of the central longitudinally directed topsheet layer section 20A. The central topsheet section 20A may be made for example, from hydrophilic TABCW materials or it may be made from a perforated film that has been treated to be hydrophilic. The lateral side topsheet sections 20B may be made from a different fibrous nonwoven material which is joined to the central longitudinally directed section 20A, such as by adhesive or thermal bonding. Such a two layer topsheet configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. It is also contemplated that such two layer topsheet materials may additionally include longitudinally extending elastic strand components (not shown) along their side edges to lift up components of the side-topsheet materials during use, thereby forming physical barriers or cupping features on the article so as to allow a fit more closely aligned to the body of a user. The liquid permeable second topsheet layer 20 is desirably in one embodiment a hydrophilic TABCW. The first and second topsheet layers may also be treated so as to impart other properties to the user-facing surface. Examples of additional treatments include application of skin health agents, coloring agents, odor control agents, stain masking agents and the like.

The additional liquid permeable topsheet layer 210 if present, may be formed from the previously described topsheet materials, although it is desirable in one embodiment that the additional liquid permeable topsheet layer 210 be a dual apertured film of a hydrophobic polyolefinic material.

The basis weight of nonwoven webs to be used as liquid permeable first, second, or additional topsheet layers may generally vary, such as from about 5 grams per square meter ("gsm") to 150 gsm, in some embodiments from about 10 gsm to about 125 gsm, and in some embodiments, from about 15 gsm to about 120 gsm. Desirably, in one embodiment, the first, second or additional topsheet layer is a through-air bonded carded web having a basis weight of between about 20 gsm and 40 gsm. In another embodiment, such liquid permeable second topsheet layer 20 is a 100 percent cotton spunlace material having a basis weight of between about 20 and 50 gsm, desirably about 30 gsm. It is desirable for the size and shape of the liquid permeable second topsheet layer 20 and liquid impermeable backsheet layers 22 to be the same, sealed together along their peripheral edges 261.

As noted, optionally a fluid transfer layer may be attached to the garment-facing surface of the liquid permeable first topsheet layer 26. Such additional fluid transfer layers include, but are not limited to, hydrophobic bonded carded webs, hydroentangled nonwoven webs, or spunbond webs.

As noted, in one embodiment, subjacent the liquid permeable second topsheet layer 20 in the article depth direction Z, is one or more interiorly situated absorbent core layers (storage component) and optional fluid management layers, designed to transport or retain body exudates that have passed through the topsheet layers.

The absorbent core layer(s) 24 can itself comprise a single layer or multiple layers and these one or more layers can themselves comprise similar or different materials. Highly absorbent core layers often include, but are not limited to, hydrophilic batts or webs containing wood pulp fibers, superabsorbent particles or fibers (also known as SAP or SAM), synthetic wood pulp fibers, synthetic fibers, coform materials, hydrophilic foam materials, and combinations thereof. The absorbent core layer may comprise any one of a number of materials and structures, the particular selection of which will vary with the desired loading capacity, flexibility, body fluid to be absorbed and other factors known to those skilled in the art. By way of example, suitable materials and/or structures for the absorbent core layers include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States patent publication 2010/0174260 to Di Luccio et al., each of which is hereby incorporated by reference thereto in its entirety.

The shape of the absorbent core layer (while generally shown as a dog-bone or oblong configuration to mimic the outer peripheral shape of the absorbent article, can vary as desired and can comprise any one of various shapes including, but not limited to, generally triangular, rectangular, dog-bone and elliptical shapes. In one embodiment, the absorbent core layer 24 has a shape that generally corresponds with the overall peripheral shape of the absorbent article such that the absorbent core layer(s) 24 terminates proximate the peripheral seal region 261. The dimensions of the absorbent core layer 24 can be substantially similar to those of the absorbent article 10, however it will be appreciated that the dimensions of the absorbent core layer 24 while similar, will often be slightly less than those of the overall absorbent article 10 in order to be adequately contained therein, and desirably sealed around the edges. Desirably in one embodiment, the absorbent core layer 24 is a spunlace web material, having a basis weight of between about 20 gsm and 80 gsm, alternatively between about 30 and 80 gsm, alternatively between about 30 gsm and 50 gsm. Such absorbent core layer 24 may in one embodiment, be constructed of a blend of synthetic fibers in a spunlace web such as for example, a blend of PET and rayon fibers, or alternatively, a homogeneous layer of 100 percent rayon fibers, air-laid materials, or foam rubber materials.

The individual layers comprising the absorbent article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis.

In a further alternative embodiment, the one or more absorbent core layers 24 can be sealed between the liquid permeable second topsheet layer 20 and the liquid impermeable backsheet layer 22 along the perimeter of the one or more absorbent core layers 24 along a peripheral seal region 261 formed by the application of heat and pressure to melt thermoplastic polymers located in the liquid permeable second topsheet layer 20 (or side sections 20B) and/or liquid impermeable backsheet layer 22. Desirably, in one embodiment, the liquid permeable second topsheet layer 20 is bonded at least at its periphery, to the liquid impermeable backsheet layer 22 at least in the peripheral seal region 261, but may also be bonded to it at other locations inward of the peripheral seal region 261, so long as such bonding does not interfere with the ability of the first topsheet layer 26 to partially separate from the second topsheet layer 20, or with liquid from flowing to the storage components (absorbent core layer 24) through the aperture opening 40, 60. In the liquid permeable second topsheet layer is to be fashioned from at least some hydrophobic materials, such are desirably limited in their placement within the layer or alternatively, the layer is desirably treated with surfactants to impart hydrophilicity to it.

The liquid impermeable backsheet layer 22 functions to isolate absorbed fluids from the wearer's garments or bedding, and therefore desirably can comprise a variety of liquid-impervious materials. In one aspect, the liquid impermeable backsheet layer 22 may optionally comprise a material that prevents the passage of liquids but allows air and water-vapor to pass there-through. The liquid impermeable backsheet layer can comprise a single layer or multiple layers, and these one or more layers can themselves comprise similar or different materials. Suitable liquid impermeable backsheet layer 22 materials include, but are not limited to, polyolefin films, nonwovens, nonwoven laminates, and film/nonwoven laminates. The particular structure and composition of the liquid impermeable backsheet layer may be selected from various known films and/or fabrics with the particular material being selected as appropriate to provide the desired level of liquid barrier, strength, abrasion resistance, tactile properties, aesthetics (such as texture and printability) and so forth. Suitable backsheet layer 22 materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety. The liquid impermeable backsheet layer 22 may be breathable or nonbreathable, as may be desired. In one embodiment, the liquid impermeable backsheet layer is a breathable polyolefinic film having a basis weight of between about 18 gsm and 40 gsm, alternatively between about 20 gsm and 30 gsm, such as of a polyethylene film.

As noted, the absorbent articles 10 of the invention may include other additional features as are generally known in the art. Such features may include wing or tab-like features 14, which are desirably extensions of the liquid permeable second topsheet layer 20 and liquid impermeable backsheet layer 22 that extend out from the opposing lateral side edges 11 of the article. Such wings 14 may also be nonintegral in construction, either being attached to the second topsheet layer 20 or the backsheet layer 22. The articles 10 may further be individually wrapped in a pouch, such as those which are commonly known in the art. In such an instance, such article 10 may be releasably fastened to the inside surface of such pouch for ease of article handling and eventual disposal.

Examples of absorbent articles that may be produced in accordance with the invention include the following:

The liquid permeable first topsheet layer may be fashioned from a 22 gsm film-nonwoven laminate. The film-nonwoven laminate may itself include at least one hydrophobic layer, including an 11 gsm micro-apertured polyolefinic film (having two sizes of micro-apertures) laminated to an 11 gsm TABCW of bicomponent fibers. A plurality of proximately located, uninterrupted circular holes of 2 mm in diameter may be arranged in the first topsheet layer through its entire thickness, arranged in a generally oval configuration (of oval dimension as previously described) along the center of the layer. This would serve to provide sufficient area for the uninterrupted fluid transfer of exudate to the liquid permeable second topsheet layer user-facing surface, and maintain integrity of the first topsheet layer. Such first topsheet layer may be attached to a hydrophilic, liquid permeable second top-sheet layer only via z folded-over edges (opposed lateral attachment zones as previously illustrated and described) to enhance elevation of the first topsheet layer over the second topsheet layer. A central longitudinal direction, embossed bend line having a width in the transverse direction of 2 mm may be positioned down the center of the first topsheet layer to help create an inverted-v fold, in order to provide more spacing in article use, to reduce the likelihood of insult on the second topsheet layer and lower absorbent layers from coming into contact with the user's skin, as well as to encourage air circulation through the pad. The length of the first topsheet layer may be desirably dimensioned such that the first topsheet layer would not itself be folded by any pad transverse direction fold lines. The second topsheet layer may be an apertured hydrophilic TABCW material having a basis weight of between about 15 gsm and 30 gsm. The absorbent article may further include a TABCW surge material positioned beneath the second topsheet layer and above the remaining layers, the surge layer having a basis weight of between about 20 gsm and 40 gsm. Such remaining layers may be an airlaid layer, having a basis weight of between about 50 gsm and 80 gsm, followed by a SAP-containing sheet having a basis weight of between about 100 gsm and 200 gsm. A polyolefinic film (PE) backsheet layer (having a basis weight of between about 20 and 30 gsm) may be sealed to the second topsheet layer at their peripheral edges.

In a second absorbent article example, a first topsheet layer may be directly attached to two other sheet materials, which all three layers may separate from, and raise above the second topsheet layer as a unit. The first topsheet layer in such an article may be an apertured polyolefinic film including macro-aperture openings of the type previously described. Such a first hydrophobic topsheet layer may be used in order to enhance dryness. A 120 gsm hydrophobic airlaid material may be situated immediately beneath the first topsheet layer (and bonded thereto), itself including a plurality of macro-aperture openings (2 mm in diameter) arranged into an oval configuration that are aligned with the aperture openings of the first topsheet layer. A 100 gsm bulky hydrophobic TABCW material with a large central oval opening (aligned with the upper layers' aperture openings) may be situated immediately beneath the airlaid material. The aperture-opening holes in each layer would allow for fluid transfer through the large central opening to the second topsheet layer, user-facing surface. The film-based, first topsheet layer and directly-attached subjacent layers may as a unit, be attached directly to the secondary topsheet layer without any z-folded edges. Such unit would be adhesively attached to the second topsheet layer at its opposing lateral side edges only. The airlaid and bulky sheet materials would be able to ultimately enhance the elevation of the first topsheet layer without the need for z folded-over edge attaching structures. The airlaid and bulky layers directly attached to the first topsheet layer would provide resiliency to the three-layer unit that would allow such unit to easily raise up above soiling on the second topsheet layer (and lower absorbent layers), thereby preventing the exudate from coming into prolonged contact with the skin, and providing for improved air circulation through the article. As with the prior example, the first topsheet layer and directly attached layers may be dimensioned so as to allow for transverse fold lines in the pad, which fold lines would not cross the first topsheet layer and directly-attached airlaid and bulky layers. In such an example, the second topsheet layer may be a hydrophilic TABCW material having a basis weight of between about 15 gsm and 30 gsm. In such example, immediately beneath the second topsheet layer may be positioned a TABCW surge material having a basis weight of between about 15 gsm and 30 gsm. A tissue-wrapped pulp fluff (having a basis weight of between about 1.6 g to 2.5 g) may serve as the storage component and be positioned between the surge layer and a polyolefinic backsheet layer as previously described.

In both of the previous examples, the second topsheet layer is a soft TABCW layer which contacts the skin of the pad user, around the peripheral edges of the first topsheet layer (and at times in the central aperture openings). Pads incorporating such TABCW nonwoven material deliver enhanced softness but typically demand higher performance in rewet. The first example of topsheet layer design serves to address the issue of dryness through an additional non-liquid retaining first topsheet layer that is elevated from the second topsheet layer, to enhance the rewet performance of the pad. The first topsheet layer is desirably of a small dimension such that it is not affected by the pad folding. It should also be of small dimension such that most of the soft second topsheet layer remains exposed to the wearer for softness and comfort. The first topsheet layer contains uninterrupted macro-aperture openings to allow efficient fluid transfer from the first topsheet layer to the secondary topsheet layer. This fluid can then be transferred to the storage component. The fact that the first topsheet layer is unattached from the second topsheet layer except at the opposing lateral side edges, creates gaps that prevent saturation from the second topsheet layer and storage component, from coming into contact with the skin, and also allows for air circulation. The second example above provides for a rigidifying structure that still allows for separation of the first topsheet layer from the second topsheet layer.

It should be understood that additional internal absorbent article layers, such as surge, transfer, and multiple absorbent core layers, can be utilized as desired within the absorbent article of the present invention subjacent to the second topsheet layer. Such additional layers are described for example in United States patent publication 2012/0277711 to Kim et al., and WO2014/085974 to Miao Lin et al., each of which are hereby incorporated by reference thereto in its entirety, for purposes consistent herewith.

As can be seen, partially separable two layer topsheets without an intermediate fluid storage component, and which separable topsheets allow for air flow between their structures, provide for both fluid acquisition quickly through uninterrupted aperture openings directly to a lower pad surface, as well as breathability and dryness over prolonged pad usage. By utilizing a relatively smaller dimensioned liquid permeable first topsheet layer, compared with a subjacent liquid permeable second topsheet layer, an easily foldable pad is created. Such smaller dimensioned liquid permeable first topsheet layer can be placed directly under the fluid insult region of a user's body such that fluid passes more directly through one or more aperture openings to the pad storage component. During use, the two topsheets continually transition from being separate to being in contact with each other due to pad deformation and pad forces exerted by the user. This constant interplay between layer contact and separation assists in reducing sensations of rewet, as air circulation is provided along the longitudinal direction of the pad, between lower layers within the pad and the upper-most, skin-contacting surface of the pad. The uppermost user-facing layer is physically separated from any immediately adjacent fluid storage component.

In one embodiment, a raised central region may be provided by an apertured lower pad layer having an aperture opening aligned with the opening of the first topsheet layer within the article. Such raised central region helps to minimize contact between the separable first and second topsheet layers outside of the article central region, and allows fluid to pass directly into a pad storage component without touching much of the upper, skin-contacting topsheet layer. By utilizing a partially separable topsheet in an absorbent article, rewet on the topsheet layer is reduced. Further, a hydrophobicity gradient between the partially separable first topsheet layer and the second topsheet layer promotes fluid transfer from the raised upper topsheet layer to the lower pad structure. Such transfer also helps to further address rewet sensations of a user of such pad.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having a longitudinal direction, a transverse direction, and a depth direction, said absorbent article having absorbent article opposing first and second longitudinal ends, and absorbent article opposing lateral side edges extending between said absorbent article opposing first and second longitudinal ends, said absorbent article comprising:
   a liquid permeable first topsheet layer having first topsheet layer opposing lateral side edges, and first topsheet layer opposing longitudinal ends;
   a liquid permeable second topsheet layer subjacent, along said absorbent article depth direction, to said liquid permeable first topsheet layer, said liquid permeable second topsheet layer having second topsheet layer opposing lateral side edges, and second topsheet layer opposing longitudinal ends, and being attached at two opposing attachment zones to said liquid permeable first topsheet layer along or adjacent said first topsheet layer opposing lateral side edges, such that said liquid permeable first topsheet layer is unattached to said liquid permeable second topsheet layer at said first topsheet layer opposing longitudinal ends, and further such that continuous unattached areas are present at least partially across the absorbent article transverse direction between said two opposing attachment zones, said first and second liquid permeable topsheet layers being unattached from one another at said continuous unattached areas;
   a liquid impermeable backsheet layer;
   at least one absorbent core layer sandwiched between said liquid permeable second topsheet layer and said liquid impermeable backsheet layer along the absorbent article depth direction;
   wherein said liquid permeable first topsheet layer is apertured such that there is at least one uninterrupted aperture opening extending through the entire thickness of said liquid permeable first topsheet layer to said liquid permeable second topsheet layer; and
   wherein said article includes an additional layer subjacent to said liquid permeable second topsheet layer in the article depth direction, said additional layer including an aperture opening that is aligned with said aperture opening of said liquid permeable first topsheet layer along the article depth direction, and is sized and shaped similarly to said first topsheet layer aperture opening.

2. The absorbent article of claim 1 wherein said liquid permeable second topsheet layer is relatively more hydrophilic than said liquid permeable first topsheet layer.

3. The absorbent article of claim 1, wherein said liquid permeable first topsheet layer includes a bend line along said absorbent article longitudinal direction.

4. The absorbent article of claim 3, wherein said liquid permeable first topsheet layer includes two side surfaces, and further wherein said bend line is an embossed line that is present on one or both side surfaces of said liquid permeable first topsheet layer.

5. The absorbent article of claim 3, wherein said absorbent article includes a central longitudinal direction, and said bend line is positioned along said central longitudinal direction.

6. The absorbent article of claim 3, wherein said at least one uninterrupted aperture opening is positioned along said bend line.

7. The absorbent article of claim 3, wherein said liquid permeable first topsheet layer includes multiple, similarly sized and shaped uninterrupted aperture openings.

8. The absorbent article of claim 3, wherein said liquid permeable first topsheet layer includes multiple, similarly shaped uninterrupted aperture openings of at least two different sizes.

9. The absorbent article of claim 3, wherein said liquid permeable first topsheet layer includes a centrally located, single oval or circular shaped, uninterrupted aperture opening.

10. The absorbent article of claim 3, wherein said liquid permeable first topsheet layer includes a user-facing, skin contacting surface and an opposing garment-facing surface, with said garment-facing surface having a non-absorbent, fluid transfer layer attached thereto.

11. The absorbent article of claim 10, wherein said fluid transfer layer includes at least one aligned aperture opening that is of the same shape and size as said at least one uninterrupted aperture opening of said fluid permeable first topsheet layer.

12. The absorbent article of claim 11, wherein said one aligned aperture opening is of a single oval or circular shape.

13. The absorbent article of claim 3, further including an additional apertured, liquid permeable topsheet layer having a longitudinal and transverse direction, said additional apertured, liquid permeable topsheet layer situated between said liquid permeable first and second topsheet layers, said additional apertured topsheet layer being attached along the full longitudinal and transverse directions of the additional apertured topsheet layer to said liquid permeable first topsheet layer.

14. The absorbent article of claim 13, wherein said additional apertured, liquid permeable topsheet layer includes multiple shaped and sized apertures.

15. The absorbent article of claim 3, wherein said liquid permeable first topsheet layer includes folds adjacent each of the first topsheet layer opposing lateral side edges.

16. The absorbent article of claim 3, wherein said liquid permeable first topsheet layer is attached to said liquid permeable second topsheet layer adjacent the second topsheet layer opposing lateral side edges, through at least one bonding method selected from the group consisting of adhesive, ultrasonic, and thermal bonding methods.

17. The absorbent article of claim 3, wherein said liquid permeable first topsheet layer includes a liquid permeable first topsheet layer, longitudinal and transverse direction, wherein said liquid permeable second topsheet layer includes a liquid permeable second topsheet layer longitudinal and transverse direction, and said liquid permeable first topsheet layer differs in dimension from said liquid permeable second topsheet layer at least along one of the transverse or longitudinal direction.

18. The absorbent article of claim 17 wherein said liquid permeable first topsheet layer differs in dimension from said liquid permeable second topsheet layer along both transverse and longitudinal directions.

19. The absorbent article of claim 18 wherein the liquid permeable first topsheet layer is shorter along the absorbent article longitudinal direction than said liquid permeable second topsheet layer.

20. The absorbent article of claim 1, wherein said liquid permeable first topsheet layer is hydrophobic.

* * * * *